(12) United States Patent
Weiskopf et al.

(10) Patent No.: US 9,945,870 B2
(45) Date of Patent: Apr. 17, 2018

(54) METHODS FOR DETERMINING RESPONSIVENESS TO AN ANTI-CD47 AGENT

(71) Applicant: The Board of Trustees of the Leland Stanford Junior University, Stanford, CA (US)

(72) Inventors: Kipp Andrew Weiskopf, Menlo Park, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/890,894

(22) PCT Filed: May 16, 2014

(86) PCT No.: PCT/US2014/038485
§ 371 (c)(1),
(2) Date: Nov. 12, 2015

(87) PCT Pub. No.: WO2014/186761
PCT Pub. Date: Nov. 20, 2014

(65) Prior Publication Data
US 2016/0069898 A1    Mar. 10, 2016

Related U.S. Application Data

(60) Provisional application No. 61/824,915, filed on May 17, 2013.

(51) Int. Cl.
*G01N 33/68* (2006.01)
*G01N 33/574* (2006.01)
*C12Q 1/68* (2006.01)

(52) U.S. Cl.
CPC ....... *G01N 33/6863* (2013.01); *C12Q 1/6883* (2013.01); *G01N 33/574* (2013.01); *C12Q 2600/106* (2013.01); *C12Q 2600/158* (2013.01); *G01N 2333/522* (2013.01); *G01N 2333/523* (2013.01); *G01N 2333/545* (2013.01); *G01N 2333/5421* (2013.01); *G01N 2333/70596* (2013.01); *G01N 2800/26* (2013.01); *G01N 2800/52* (2013.01)

(58) Field of Classification Search
CPC ............ G01N 33/574; G01N 33/6863; G01N 2333/522; G01N 2333/523; G01N 2333/5421; G01N 2333/545; G01N 2333/70596; G01N 2800/26; G01N 2800/52; C12Q 1/6883; C12Q 2600/106; C12Q 2600/158
See application file for complete search history.

(56) References Cited

U.S. PATENT DOCUMENTS

2010/0203010 A1   8/2010   Hariharan et al.
2012/0282174 A1   11/2012  Weissman et al.

FOREIGN PATENT DOCUMENTS

WO   2013/112942   8/2013

OTHER PUBLICATIONS

Majeti et al. 'CD47 is an adverse prognostic factor and therapeutic antibody target on human acute myeloid leukemia stem cells,' Cell, Jul. 23, 2009 (Jul. 23, 2009), vol. 138, pp. 286-299.
Demeure et al. 'CD47 Engagement Inhibits Cytokine Production and Maturation of Human Dendritic Cells,' J Immunol, Feb. 15, 2000 (Feb. 15, 2000), vol. 164, pp. 2193-2199.

*Primary Examiner* — Robert S Landsman
(74) *Attorney, Agent, or Firm* — Pamela J. Sherwood; Bozicevic, Field & Francis LLP

(57) ABSTRACT

Methods and kits are provided for determining whether an individual is responsive to an anti-CD47 agent and for determining whether an individual is maintaining responsiveness to an anti-CD47 agent by assaying biological samples for the level of at least one biomarker in a biological sample.

20 Claims, 12 Drawing Sheets

METHODS FOR DETERMINING RESPONSIVENESS TO AN ANTI-CD47 AGENT

GOVERNMENT RIGHTS

This invention was made with Government support under contracts CA168059, CA139490 and CA086017 awarded by the National Institutes of Health. The Government has certain rights in the invention.

BACKGROUND OF THE INVENTION

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Unlike healthy cells, the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells, are present in an altered conformation or they are superseded by the upregulation of "eat-me" or pro-phagocytic signals. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Blocking SIRPα also allows engulfment of targets that are not normally phagocytosed, for those cells where pro-phagocytic signals are also present.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. July 25; 31(2):266-77; Hatherley et al. (2007) J. B. C. 282:14567-75; and the role of SIRPα cis dimerization in CD47 binding is discussed by Lee et al. (2010) J. B. C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

Programmed cell death (PCD) and phagocytic cell removal are common ways that an organism responds in order to remove damaged, precancerous, or infected cells. Thus, the cells that survive this organismal response (e.g., cancerous cells, chronically infected cells, etc.) have devised ways to evade PCD and phagocytic cell removal. CD47, the "don't eat me" signal, is constitutively upregulated on a wide variety of diseased cells, cancer cells, and infected cells, allowing these cells to evade phagocytosis. Anti-CD47 agents that block the interaction between CD47 on one cell (e.g., a cancer cell, an infected cell, etc.) and SIRPα on another cell (e.g., a phagocytic cell) counteract the increase of CD47 expression and facilitate the phagocytosis of the cancer cell and/or the infected cell.

Anti-CD47 agents can be used to treat and/or protect against a wide variety of conditions/disorders. Because many of these conditions/disorders can be life-threatening, it is important to evaluate after the administration of an anti-CD47 agent whether a particular individual and/or a particular condition (e.g., a disease condition) is responsive to the treatment. The present invention provides methods to determine whether an individual is responsive to an anti-CD47 agent (i.e., responsive to treatment with an anti-CD47 agent), thereby enabling the determination of whether the treatment should be continued or altered.

PUBLICATIONS

Bandow K et al., FEBS Lett. 2012 May 21; 586(10):1540-6: "LPS-induced chemokine expression in both MyD88-dependent and -independent manners is regulated by Cot/Tpl2-ERK axis in macrophages."

Lazzarino et al., Cytokine. 2001 May 21; 14(4):234-9: "IL-8 and MCP-1 secretion is enhanced by the peptide-nucleic acid immunomodulator, Product R, in U937 cells and primary human monocytes."

Majeti et al., Cell 2009 Jul. 23; 138(2):286-99: "CD47 is an adverse prognostic factor and therapeutic antibody target on human acute myeloid leukemia stem cells."

Sherry B et al., J Exp Med. 1988 Dec. 1; 168(6):2251-9: "Resolution of the two components of macrophage inflammatory protein 1, and cloning and characterization of one of those components, macrophage inflammatory protein 1 beta."

Sintes et al., J Leukoc Biol. 2010 October; 88(4):687-97: "Mouse CD84 is a pan-leukocyte cell-surface molecule that modulates LPS-induced cytokine secretion by macrophages."

Thirion et al., Biochem Biophys Res Commun. 1994 Jun. 15; 201(2):493-9: "Mouse macrophage derived monocyte chemotactic protein-3: cDNA cloning and identification as MARC/FIC."

Wolpe S D et al., J Exp Med. 1988 Feb. 1; 167(2):570-81: "Macrophages secrete a novel heparin-binding protein with inflammatory and neutrophil chemokinetic properties."

SUMMARY OF THE INVENTION

Methods are provided for determining whether an individual is responsive to an anti-CD47 agent and for determining whether an individual is maintaining responsiveness to an anti-CD47 agent. In the subject methods, pre-treatment and post-treatment biological samples isolated from an individual are assayed to determine the level of a biomarker, where the level of the biomarker correlates with the individual's responsiveness to the administration of an anti-CD47 agent. In some embodiments, the methods of the invention find use in determining whether to continue or alter therapy. In some such embodiments, the individual is being treated with an anti-CD47 agent for cancer. In other embodiments the individual is being treated with an anti-CD47 agent for infection, particularly with an intracellular pathogen.

Positive biomarkers increase in expression when an individual is responsive to the administration of an anti-CD47 agent. Suitable positive biomarkers include MCP-3, MCP-1, IL-1A, IL-8, MIP-1α, MIP-1β, and MIG. Negative biomarkers decrease in expression when an individual is responsive to the administration of an anti-CD47 agent. Suitable negative biomarkers include IL12p40. Neutral biomarkers do not significantly change in expression when an individual is responsive to the administration of an anti-CD47 agent. Suitable neutral biomarkers include IL12P70, IL-1β, IL-6, and TNFα.

Any biological sample can be assayed to determine the level of a biomarker. Suitable biological samples include: a blood sample, a serum sample, a plasma sample, a biopsy sample, a fine needle aspirate, a lymph node aspirate, a cystic aspirate, a paracentesis sample, a thoracentesis sample, and the like. In some cases, the level of protein of a biomarker is measured. In some cases, the level of mRNA of a biomarker is measured.

In some embodiments of the invention, two or more anti-CD47 agents are administered. In some embodiments, an anti-CD47 agent is administered more than once. In some cases, the subject methods can be used to determine whether an individual is responsive to prolonged treatment with an anti-CD47 agent.

An anti-CD47 agent for use in the methods of the invention interferes with binding between CD47 present on a target cell, including without limitation a cancer cell, a cell infected with an intracellular pathogen, a stem cell, etc., to SIRPα present on a phagocytic cell. Generally both such cells are present in the individual being treated. Such methods, in the presence of a pro-phagocytic signal, can increase phagocytosis of the target cell. The subject methods can be used to monitor the treatment of an individual for any disease susceptible to blockade of CD47-mediated SIRPα signaling. Suitable anti-CD47 agents include soluble SIRPα polypeptides; soluble CD47; anti-CD47 antibodies, anti-SIRPα antibodies, small molecules, and the like, where the term antibodies encompasses antibody fragments and variants thereof, as known in the art.

DETAILED DESCRIPTION OF THE INVENTION

Figure 1A:
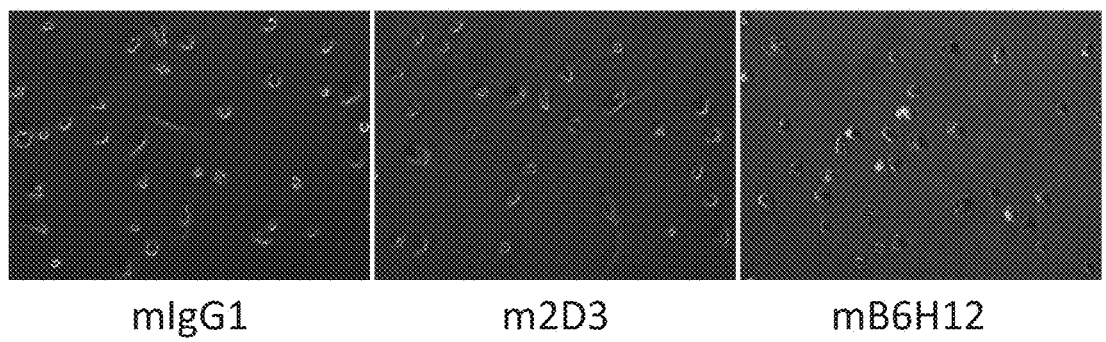
FIG. 1A-1B CD47-blocking therapies induced phagocytosis of cancer cells

The present invention relates to methods of determining whether an individual is responsive to an anti-CD47 agent and methods of determining whether an individual is maintaining responsiveness to an anti-CD47 agent comprising assaying biological samples for the level of at least one biomarker. The present invention further relates to kits for performing the methods.

Before the present methods and kits are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Biological sample. The term "sample" with respect to an individual encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample. The types of "biological samples" include, but are not limited to: tissue obtained by surgical resection, tissue obtained by biopsy, cells in culture, cell supernatants, cell lysates, tissue samples, organs, bone marrow, blood, plasma, serum, fine needle aspirate, lymph node aspirate, cystic aspirate, a paracentesis sample, a thoracentesis sample, and the like. A "biological sample" can include cells (e.g., target cells, normal cells, blood cells, tissue cells etc.) can be suspected of comprising such cells, or can be devoid of cells. A biological sample can include biological fluids derived from cells (e.g., a cancerous cell, an infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells. In some embodiments the biological sample is blood or a derivative thereof, e.g. plasma, serum, etc.

Obtaining and assaying a sample. The term "assaying" is used herein to include the physical steps of manipulating a biological sample to generate data related to the sample. As will be readily understood by one of ordinary skill in the art, a biological sample must be "obtained" prior to assaying the sample. Thus, the term "assaying" implies that the sample has been obtained. The terms "obtained" or "obtaining" as used herein encompass the act of receiving an extracted or isolated biological sample. For example, a testing facility can "obtain" a biological sample in the mail (or via delivery, etc.) prior to assaying the sample. In some such cases, the biological sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample.

The terms "obtained" or "obtaining" as used herein can also include the physical extraction or isolation of a biological sample from a subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

It will be understood by one of ordinary skill in the art that in some cases, it is convenient to wait until multiple samples (e.g., a pre-treatment biological sample and a post-treatment biological sample) have been obtained prior to assaying the samples. Accordingly, in some cases an isolated biological sample (e.g., a pre-treatment biological sample, a post-treatment biological sample, etc.) is stored until all appropriate samples have been obtained. One of ordinary skill in the art will understand how to appropriately store a variety of different types of biological samples and any convenient method of storage may be used (e.g., refrigeration) that is appropriate for the particular biological sample. In some embodiments, a pre-treatment biological sample is assayed prior to obtaining a post-treatment biological sample. In some cases, a pre-treatment biological sample and a post-treatment biological sample are assayed in parallel. In some cases, multiple different post-treatment biological samples and/or a pre-treatment biological sample are assayed in parallel. In some cases, biological samples are processed immediately or as soon as possible after they are obtained.

In subject methods, the concentration (i.e., "level"), or expression level of a gene product, which may be an RNA, a protein, etc., (which will be referenced herein as a biomarker), in a biological sample is measured (i.e., "determined"). By "expression level" (or "level") it is meant the level of gene product (e.g. the absolute and/or normalized value determined for the RNA expression level of a biomarker or for the expression level of the encoded polypeptide, or the concentration of the protein in a biological sample). The term "gene product" or "expression product" are used herein to refer to the RNA transcription products (RNA transcripts, e.g. mRNA, an unspliced RNA, a splice variant mRNA, and/or a fragmented RNA) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assaying may be relative or absolute. For example, "assaying" can be determining whether the expression level is less than or "greater than or equal to" a particular threshold, (the threshold can be pre-determined or can be determined by assaying a control sample). On the other hand, "assaying to determine the expression level" can mean determining a quantitative value (using any convenient metric) that represents the level of expression (i.e., expression level, e.g., the amount of protein and/or RNA, e.g., mRNA) of a particular biomarker. The level of expression can be expressed in arbitrary units associated with a particular assay (e.g., fluorescence units, e.g., mean fluorescence intensity (MFI)), or can be expressed as an absolute value with defined units (e.g., number of mRNA transcripts, number of protein molecules, concentration of protein, etc.). Additionally, the level of expression of a biomarker can be compared to the expression level of one or more additional genes (e.g., nucleic acids and/or their encoded proteins) to derive a normalized value that represents a normalized expression level. The specific metric (or units) chosen is not crucial as long as the same units are used (or conversion to the same units is performed) when evaluating multiple biological samples from the same individual (e.g., biological samples taken at different points in time from the same individual). This is because the units cancel when calculating a fold-change (i.e., determining a ratio) in the expression level from one biological sample to the next (e.g., biological samples taken at different points in time from the same individual).

For measuring RNA levels, the amount or level of an RNA in the sample is determined, e.g., the level of an mRNA. In some instances, the expression level of one or more additional RNAs may also be measured, and the level of biomarker expression compared to the level of the one or more additional RNAs to provide a normalized value for the biomarker expression level. Any convenient protocol for evaluating RNA levels may be employed wherein the level of one or more RNAs in the assayed sample is determined.

A number of exemplary methods for measuring RNA (e.g., mRNA) expression levels (e.g., expression level of a nucleic acid biomarker) in a sample are known by one of ordinary skill in the art, and any convenient method can be used. Exemplary methods include, but are not limited to: hybridization-based methods (e.g., Northern blotting, array hybridization (e.g., microarray); in situ hybridization; in situ hybridization followed by FACS; and the like)(Parker & Barnes, Methods in Molecular Biology 106:247-283 (1999)); RNAse protection assays (Hod, Biotechniques 13:852-854 (1992)); PCR-based methods (e.g., reverse transcription PCR (RT-PCR), quantitative RT-PCR (qRT-PCR), real-time RT-PCR, etc.)(Weis et al., Trends in Genetics 8:263-264 (1992)); nucleic acid sequencing methods (e.g., Sanger sequencing, Next Generation sequencing (i.e., massive parallel high throughput sequencing, e.g., Illumina's reversible terminator method, Roche's pyrosequencing method (454), Life Technologies' sequencing by ligation (the SOLiD platform), Life Technologies' Ion Torrent platform, single molecule sequencing, etc.); and the like.

In some embodiments, the biological sample can be assayed directly. In some embodiments, nucleic acid of the biological sample is amplified (e.g., by PCR) prior to assaying. As such, techniques such as PCR (Polymerase Chain Reaction), RT-PCR (reverse transcriptase PCR), qRT-PCR (quantitative RT-PCR, real time RT-PCR), etc. can be used prior to the hybridization methods and/or the sequencing methods discussed above.

For measuring mRNA levels, the starting material is typically total RNA or poly A+ RNA isolated from a biological sample (e.g., suspension of cells from a peripheral blood sample, a bone marrow sample, etc., or from a homogenized tissue, e.g. a homogenized biopsy sample, an aspirate, a homogenized paraffin- or OCT-embedded sample, etc.). General methods for mRNA extraction are well known in the art and are disclosed in standard textbooks of molecular biology, including Ausubel et al., Current Protocols of Molecular Biology, John Wiley and Sons (1997). RNA isolation can also be performed using a purification kit, buffer set and protease from commercial manufacturers, according to the manufacturer's instructions. For example, RNA from cell suspensions can be isolated using Qiagen RNeasy mini-columns, and RNA from cell suspensions or homogenized tissue samples can be isolated using the TRIzol reagent-based kits (Invitrogen), MasterPure™ Complete DNA and RNA Purification Kit (EPICENTRE™, Madison, Wis.), Paraffin Block RNA Isolation Kit (Ambion, Inc.) or RNA Stat-60 kit (Tel-Test).

A variety of different manners of measuring mRNA levels are known in the art, e.g. as employed in the field of differential gene expression analysis. One representative and convenient type of protocol for measuring mRNA levels is array-based gene expression profiling. Such protocols are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Alternatively, non-array based methods for quantitating the level of one or more nucleic acids in a sample may be employed. These include those based on amplification protocols, e.g., Polymerase Chain Reaction (PCR)-based assays, including quantitative PCR, reverse-transcription PCR (RT-PCR), real-time PCR, and the like, e.g. TaqMan® RT-PCR, MassARRAY® System, BeadArray® technology, and Luminex® technology; and those that rely upon hybridization of probes to filters, e.g. Northern blotting and in situ hybridization.

Examples of some of the nucleic acid sequencing methods listed above are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps.

For measuring protein levels, the amount or level of a polypeptide in the biological sample is determined. In some embodiments, the extracellular protein level is measured. For example, in some cases, the protein (i.e., polypeptide) being measured is a secreted protein (e.g., a cytokine or chemokine) and the concentration can therefore be measured in the extracellular fluid of a biological sample (e.g., the concentration of a protein can be measured in the serum). In some embodiments concentration is a relative value measured by comparing the level of one protein relative to another protein. In other embodiments the concentration is an absolute measurement of weight/volume or weight/weight.

In some cases, the cells are removed from the biological sample (e.g., via centrifugation, via adhering cells to a dish or to plastic, etc.) prior to measuring the concentration. In some cases, the intracellular protein level is measured by lysing the removed cells of the biological sample to measure the level of protein in the cellular contents. In some cases, both the extracellular and intracellular levels of protein are measured by separating the cellular and fluid portions of the biological sample (e.g., via centrifugation), measuring the extracellular level of the protein by measuring the level of protein in the fluid portion of the biological sample, and measuring the intracellular level of protein by measuring the level of protein in the cellular portion of the biological sample (e.g., after lysing the cells). In some cases, the total level of protein (i.e., combined extracellular and intracellular protein) is measured by lysing the cells of the biological sample to include the intracellular contents as part of the sample.

In some instances, the concentration of one or more additional proteins may also be measured, and biomarker concentration compared to the level of the one or more additional proteins to provide a normalized value for the biomarker concentration. Any convenient protocol for evaluating protein levels may be employed wherein the level of one or more proteins in the assayed sample is determined.

While a variety of different manners of assaying for protein levels are known to one of ordinary skill in the art and any convenient method may be used, one representative and convenient type of protocol for assaying protein levels is ELISA, an antibody-based method. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Following incubation, the antisera-contacted surface is washed so as to remove non-immunocomplexed material. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzthiazoline)-6-sulfonic acid (ABTS) and H2O2, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody. The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatograpic column or filter with a wash solution or solvent.

Alternatively, non-ELISA based-methods for measuring the levels of one or more proteins in a sample may be employed. Representative exemplary methods include but are not limited to antibody-based methods (e.g., Western blotting, proteomic arrays, xMAP™ microsphere technology (e.g., Luminex® technology), immunohistochemistry, flow cytometry, and the like) as well as non antibody-based methods (e.g., mass spectrometry).

Biomarkers. The term "biomarker" as used herein means a gene product, i.e. protein or RNA, whose concentration (i.e., "level") reports the activity of an administered anti-CD47 agent. Because some individuals may not be responsive to treatment with an anti-CD47 agent, a biomarker can be used to determine whether an anti-CD47 agent has the desired effect in an individual (e.g., determining whether the individual is responsive to the anti-CD47 agent, determining whether the individual is maintaining responsiveness to the anti-CD47 agent, etc.). For example, a biomarker whose level increases upon administration of an anti-CD47 agent when an individual is responsive to the anti-CD47 agent is a "positive biomarker"; a biomarker whose level decreases upon administration of an anti-CD47 agent when an individual is responsive to the anti-CD47 agent is a "negative biomarker"; and a biomarker whose level does not change upon administration of an anti-CD47 agent when an individual is responsive to the anti-CD47 agent is a "neutral biomarker."

In some embodiments, the concentration or level of a biomarker is determined before and after the administration of an anti-CD47 agent and the degree of change, or lack thereof, is interpreted as an indication of whether an administered anti-CD47 agent is in fact blocking the interaction between CD47 and SIRPα, and/or whether this blockade has the desired effect (i.e., whether the immune system, e.g., phagocytes, has been activated in response to contact with or administration of an anti-CD47 agent). In other words, the concentration or level of a biomarker is determined before and after the administration of an anti-CD47 agent to an individual and the degree of change, or lack thereof, of level is interpreted as an indication of whether the individual is "responsive" to the anti-CD47 agent and/or whether the individual is "maintaining responsiveness" to the anti-CD47 agent.

A "positive biomarker" is a biomarker whose level increases in response to contact and/or treatment with an anti-CD47 agent when an individual and/or cell is responsive to the anti-CD47 agent. As such, a biological sample isolated from an individual to whom an anti-CD47 agent has been administered exhibits an increased level of a positive biomarker (relative to the level of the same biomarker measured from the same type of biological sample from the same individual prior to the administration of the anti-CD47 agent) if the anti-CD47 agent is having the desired effect. In some embodiments, the level of a positive biomarker increases by about 1.5-fold or more (e.g., 2-fold or more, 2.5-fold or more, 3-fold or more, 3.5-fold or more, 4-fold or more, 4.5-fold or more, or 5-fold or more, 8-fold or more, 10-fold or more, 15-fold or more) in response to contact and/or treatment with an anti-CD47 agent when an individual and/or cell is responsive to the anti-CD47 agent.

Positive biomarkers include, but are not necessarily limited to: MCP-3 (Monocyte Chemoattractant Protein 3, MCP3; also known as CCL7; SEQ ID NO:1), MCP-1 (Monocyte Chemoattractant Protein 1, MCP1; also known as CCL2; SEQ ID NO:2), IL-1A (Interleukin-1 alpha, IL1A, IL1α, IL-1α; SEQ ID NO:3), IL-8 (Interleukin 8, IL8; SEQ ID NO:4), MIP-1α (Macrophage Inflammatory Protein 1-alpha, MIP1α; also known as CCL3; SEQ ID NO:5), MIP-1β(Macrophage Inflammatory Protein 1-beta, MIP1β; also known as CCL4; SEQ ID NO:6), and MIG (Monokine Induced by Gamma Interferon; also known as CXCL9; SEQ ID NO:7). The level of any combination of the above positive biomarkers can be measured and utilized in the subject methods.

A "negative biomarker" is a biomarker whose level decreases in response to contact and/or treatment with an anti-CD47 agent when an individual and/or cell is responsive to the anti-CD47 agent. As such, a biological sample isolated from an individual to whom an anti-CD47 agent has been administered exhibits a decreased level of a negative biomarker (relative to the level of the same biomarker measured from the same type of biological sample from the same individual prior to the administration of the anti-CD47 agent) if the anti-CD47 agent is having the desired effect. In some embodiments, the level of a negative biomarker decreases by about 1.5-fold or more (e.g., 2-fold or more, 2.5-fold or more, 3-fold or more, 3.5-fold or more, 4-fold or more, 4.5-fold or more, or 5-fold or more, 8-fold or more, 10-fold or more, 15-fold or more) in response to contact and/or treatment with an anti-CD47 agent when an individual and/or cell is responsive to the anti-CD47 agent. Negative biomarkers include, but are not necessarily limited to: IL12p40 (Interleukin 12 Subunit p40, IL-12-p40, IL-12p40, IL12-p40; also known as interleukin 12B (IL12B); SEQ ID NO:8).

A "neutral biomarker" is a biomarker whose level does not significantly increase or decrease in response to contact and/or treatment with an anti-CD47 agent when an individual and/or cell is responsive to the anti-CD47 agent. The term "neutral biomarker" is used to refer to a protein or RNA whose level may have been expected to change (e.g., because the level of the gene changes in other contexts that alter an individual's immune state, e.g., during an inflammatory response), but was experimentally shown not to change in a context where an anti-CD47 agent is used to block the interaction between CD47 and SIRPα. As such, a biological sample isolated from an individual to whom an anti-CD47 agent has been administered exhibits a similar level of a neutral biomarker (relative to the level of the same biomarker measured from the same type of biological sample from the same individual prior to the administration of the anti-CD47 agent or to a standardized control) if the anti-CD47 agent is having the desired effect. In some embodiments, the level of a neutral biomarker changes less than about 5-fold (e.g., less than about 4.5-fold, less than about 4-fold, less than about 3.5-fold, less than about 3-fold, less than about 2.5-fold, less than about 2-fold, or less than about 1.5-fold) in response to contact and/or treatment with an anti-CD47 agent when an individual and/or cell is responsive to the anti-CD47 agent. Neutral biomarkers include, but are not necessarily limited to: IL12P70 (Interleukin-12 P70, IL-12p70, IL-12-p70, IL12-p70; a heterodimeric cytokine composed of two covalently linked Interleukin-12 chains, p40 and p35), IL-1β(Interleukin-1 beta, IL1β; SEQ ID NO:9), IL-6 (Interleukin-6, IL6; also known as interferon beta-2; SEQ ID NO:10), and TNFα (Tumor necrosis factor alpha; SEQ ID NO:11). The level of any combination of the above neutral biomarkers can be measured and utilized in the subject methods.

Anti-CD47 agent. As used herein, the term "anti-CD47 agent" or "CD47-blocking agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1 2004). Thus, in some embodiments, the anti-CD47 agent does not directly induce cell death of a CD47-expressing cell.

Some pathogens (e.g., pox viruses, Myxoma virus, Deerpox virus, swinepox virus, goatpox virus, sheeppox virus, etc.) express a CD47-analog (i.e., a CD47 mimic) (e.g., the M128L protein) that acts as a virulence factor to enable infection (Cameron et al., Virology. 2005 Jun. 20; 337(1): 55-67), and some pathogens induce the expression of endogenous CD47 in the host cell. Cells infected with a pathogen that expresses a CD47-analog may therefore express the pathogen-provided CD47 analog either exclusively or in combination with endogenous CD47. This mechanism allows the pathogen to increase CD47 expression (via expression of the CD47 analog) in the infected cell with or without increasing the level of endogenous CD47. In some embodiments, an anti-CD47 agent (e.g., anti-CD47 antibody, a SIRPα reagent, a SIRPα antibody, a soluble CD47 polypeptide, etc.) can reduce the binding of a CD47 analog (i.e., a CD47 mimic) to SIRPα. In some cases, a suitable anti-CD47 agent (e.g., a SIRPα reagent, an anti-CD47 antibody, etc.) can bind a CD47 analog (i.e., a CD47 mimic) to reduce the binding of the CD47 analog to SIRPα. In some cases, a suitable anti-CD47 agent (e.g., an anti-SIRPα antibody, a soluble CD47 polypeptide, etc.) can bind to SIRPα. A suitable anti-CD47 agent that binds SIRPα does not activate SIRPα (e.g., in the SIRPα-expressing phagocytic cell). An anti-CD47 agent can be used in any of the methods provided herein when the pathogen is a pathogen that provides a CD47 analog. In other words the term "CD47," as used herein, encompasses CD47 as well as CD47 analogs (i.e., CD47 mimics).

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof (e.g., CV1-hIgG4). High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". A non-limiting example of a non-blocking antibody is anti-CD47 antibody 2D3, which binds to CD47, but does not reduce the interaction between CD47 and SIRPα. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide (SEQ ID NO:2), such that the extracellular portion of CD47 is typically 142 amino acids in length, and has the amino acid sequence set forth in SEQ ID NO:3. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. In an exemplary embodiment, the CD47 extracellular domain lacking the signal peptide has the amino acid sequence set forth in SEQ ID NO:1 (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to SEQ ID NO:1.

Additional terms. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

A target cell may be a cell that is "inflicted", where the term "inflicted" is used herein to refer to a subject with symptoms, an illness, or a disease that can be treated with an anti-CD47 agent. An "inflicted" subject can have cancer, can harbor an infection (e.g., a chronic infection), and other hyper-proliferative conditions, for example sclerosis, fibrosis, and the like, etc. "Inflicted cells" may be those cells that cause the symptoms, illness, or disease. As non-limiting examples, the inflicted cells of an inflicted patient can be cancer cells, infected cells, and the like. One indication that an illness or disease can be treated with an anti-CD47 agent is that the involved cells (i.e., the inflicted cells, e.g., the cancerous cells, the infected cells, etc.) express an increased level of CD47 compared to normal cells of the same cell type.

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

Examples of symptoms, illnesses, and/or diseases that can be treated with an anti-CD47 agent include, but are not limited to cancer and infection (e.g., chronic infection). As used herein "cancer" includes any form of cancer (e.g., leukemia; acute myeloid leukemia (AML); acute lymphoblastic leukemia (ALL); metastasis; minimal residual disease; solid tumor cancers, e.g., lung, prostate, breast, bladder, colon, ovarian, glioblastoma, medulloblastoma, leiomyosarcoma, and head & neck squamous cell carcinomas, melanomas; etc.). Any cancer, where the cancer cells exhibit increased expression of CD47 or pro-phagocytic "eat me" signals compared to non-cancer cells, is a suitable cancer to be treated by the subject methods and kits.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces increased CD47 expression or upregulation of pro-phagocytic "eat me" signals in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of an anti-CD47 agent is an amount that is sufficient to palliate, ameliorate, stabilize, reverse, prevent, slow or delay the progression of the disease state (e.g., cancer or chronic infection) by increasing phagocytosis of a target cell (e.g., a target cell). Thus, a therapeutically effective dose of an anti-CD47 agent reduces the binding of CD47 on a target cell, to SIRPα on a phagocytic cell, at an effective dose for increasing the phagocytosis of the target cell.

In some embodiments, a therapeutically effective dose is one that provides for sustained serum levels of anti-CD47 agent (e.g., an anti-CD47 antibody) of about 40 μg/ml or more (e.g., about 50 ug/ml or more, about 60 ug/ml or more, about 75 ug/ml or more, about 100 ug/ml or more, about 125 ug/ml or more, or about 150 ug/ml or more). In some embodiments, a therapeutically effective dose leads to sustained serum levels of anti-CD47 agent (e.g., an anti-CD47 antibody) that range from about 40 μg/ml to about 300 ug/ml (e.g., from about 40 ug/ml to about 250 ug/ml, from about 40 ug/ml to about 200 ug/ml, from about 40 ug/ml to about 150 ug/ml, from about 40 ug/ml to about 100 ug/ml, from about 50 ug/ml to about 300 ug/ml, from about 50 ug/ml to about 250 ug/ml, from about 50 ug/ml to about 200 ug/ml, from about 50 ug/ml to about 150 ug/ml, from about 75 ug/ml to about 300 ug/ml from about 75 ug/ml to about 250 ug/ml, from about 75 ug/ml to about 200 ug/ml, from about 75 ug/ml to about 150 ug/ml, from about 100 ug/ml to about 300 ug/ml, from about 100 ug/ml to about 250 ug/ml, or from about 100 ug/ml to about 200 ug/ml). In some embodiments, a therapeutically effective dose for treating solid tumors provides for sustained serum levels of anti-CD47 agent (e.g., an anti-CD47 antibody) of about 100 μg/ml or more (e.g., sustained serum levels that range from about 100 ug/ml to about 200 ug/ml). In some embodiments, a therapeutically effective dose for treating non-solid tumors (e.g., acute myeloid leukemia (AML)) provides for sustained serum levels of anti-CD47 agent (e.g., an anti-CD47 antibody) of about 50 μg/ml or more (e.g., sustained serum levels of 75 μg/ml or more; or sustained serum levels that range from about 50 ug/ml to about 150 ug/ml).

Accordingly, a single therapeutically effective dose or a series of therapeutically effective doses would be able to achieve and maintain a serum level of anti-CD47 agent. A therapeutically effective dose of an anti-CD47 agent can depend on the specific agent used, but is usually about 2 mg/kg body weight or more (e.g., about 2 mg/kg or more, about 4 mg/kg or more, about 8 mg/kg or more, about 10 mg/kg or more, about 15 mg/kg or more, about 20 mg/kg or more, about 25 mg/kg or more, about 30 mg/kg or more, about 35 mg/kg or more, or about 40 mg/kg or more), or from about 10 mg/kg to about 40 mg/kg (e.g., from about 10 mg/kg to about 35 mg/kg, or from about 10 mg/kg to about 30 mg/kg). The dose required to achieve and/or maintain a particular serum level is proportional to the amount of time between doses and inversely proportional to the number of doses administered. Thus, as the frequency of dosing increases, the required dose decreases. The optimization of dosing strategies will be readily understood and practiced by one of ordinary skill in the art.

A sub-therapeutic dose is a dose (i.e., an amount) that is not sufficient to effect the desired clinical results. For example, a sub-therapeutic dose of an anti-CD47 agent is an amount that is not sufficient to palliate, ameliorate, stabilize, reverse, prevent, slow or delay the progression of the disease state (e.g., cancer, infection, inflammation, etc.). In some cases, it is desirable to use a sub-therapeutic dose of an anti-CD47 agent as a primer agent (described in more detail below). While the use of a sub-therapeutic dose of an anti-CD47 agent as a primer agent achieves a desired outcome (e.g., the subject is "primed" to receive a therapeutically effective dose), the dose is not considered to be a "therapeutic dose" because the sub-therapeutic dose does not effectively increase phagocytosis of a target cell and is not sufficient to palliate, ameliorate, stabilize, reverse, prevent, slow or delay the progression of the disease state. A sub-therapeutic dose of an anti-CD47 agent can depend on the specific agent used, but is generally less than about 10 mg/kg.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, or binding of a SIRPα polypeptide). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 and/or SIRPα (i.e., anti-CD47 agents), or that otherwise block the interaction between CD47 and SIRPα.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The terms "phagocytic cells" and "phagocytes" are used interchangeably herein to refer to a cell that is capable of phagocytosis. There are three main categories of phagocytes: macrophages and mononuclear cells (histiocytes and monocytes); polymorphonuclear leukocytes (neutrophils); and dendritic cells.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Providing an analysis" is used herein to refer to the delivery of an oral or written analysis (i.e., a document, a report, etc.). A written analysis can be a printed or electronic document. A suitable analysis (e.g., an oral or written report) provides any or all of the following information: identifying information of the subject (name, age, etc.), a description of what type of biological sample(s) was used and/or how it was used, the technique used to assay the sample, the results of the assay (e.g., the level of the biomarker as measured in the pre-treatment and post-treatment biological samples and/or the fold-change of a biomarker level in a post-treatment biological sample compared to a pre-treatment biological sample), the assessment as to whether the individual is determined to be responsive or not responsive to the anti-CD47 agent, the assessment as to whether the individual is determined to be maintaining responsiveness or not maintaining responsiveness to the anti-CD47 agent, a recommendation to continue or alter therapy, a recommended strategy for additional therapy, etc. The report can be in any format including, but not limited to printed information on a suitable medium or substrate (e.g., paper); or electronic format. If in electronic format, the report can be in any computer readable medium, e.g., diskette, compact disk (CD), flash drive, and the like, on which the information has been recorded. In addition, the report may be present as a website address which may be used via the internet to access the information at a remote site.

Methods

Methods are provided for determining whether an individual is responsive to an anti-CD47 agent and for determining whether an individual is maintaining responsiveness to an anti-CD47 agent. The subject methods include a step of assaying a pre-treatment biological sample and a post-treatment biological sample isolated from the individual to determine the level of a biomarker in the pre-treatment and post-treatment biological samples. The level of a biomarker in the pre-treatment biological sample can be referred to as a "pre-treatment value" because the first biological sample is isolated from the individual prior to the administration of an anti-CD47 agent (i.e., "pre-treatment"). The level of a biomarker in the pre-treatment biological sample can also be referred to as a "baseline value" because this value is the value to which "post-treatment expression" values are compared. In some cases, the baseline value (i.e., "pre-treatment value") is determined by determining the level of a biomarker from multiple (i.e., more than one, e.g., two or more, three or more, for or more, five or more, etc.) pre-treatment biological samples. In some cases, the multiple pre-treatment biological samples are isolated from an individual at different time points in order to assess natural fluctuations in biomarker level prior to treatment. As such, in some cases, one or more (e.g., two or more, three or more, for or more, five or more, etc.) pre-treatment biological samples are isolated from the individual. In some embodiments, all of the pre-treatment biological samples will be the same type of biological sample (e.g., a blood sample, a serum sample, a plasma sample, a biopsy sample, an aspirate, etc.). In some cases, two or more pre-treatment biological samples are pooled prior to determining the level of the biomarker. In some cases, the level of the biomarker is determined separately for two or more pre-treatment biological samples and a "pre-treatment value" is calculated by averaging the separate measurements.

A post-treatment biological sample is isolated from an individual after the administration of an anti-CD47 agent. Thus, the level of a biomarker in a post-treatment sample can be referred to as a "post-treatment value". In some embodiments, additional post-treatment biological samples (e.g., a second, third, fourth, fifth, etc. post-treatment biological sample) are assayed to determine the level of a biomarker in that sample. Because additional post-treatment biological samples are isolated from the individual after the administration of an anti-CD47 agent, the levels of a biomarker in the additional biological samples can also be referred to as "post-treatment values."

The subject methods include a step of assaying pre-treatment and post-treatment biological samples isolated from an individual to determine the level of one or more of a positive biomarker (e.g., MCP-3, MCP-1, IL-1A, IL-8, MIP-1α, MIP-1β, and/or MIG); and/or a negative biomarker (e.g., IL12p40), and/or one or more of a neutral biomarker (e.g., IL12p70, IL-1β, IL-6, and/or TNFα). The levels are then compared to determine whether the individual is responsive or not responsive to the anti-CD47 agent; or to determine whether the individual is maintaining or not maintaining responsiveness to the anti-CD47 agent.

Because the level of a positive biomarker increases as a result of administering an anti-CD47 agent when an individual is responsive to the anti-CD47 agent (see working examples below), an increase in the level of a positive biomarker indicates that the individual is responsive or is maintaining responsiveness to an anti-CD47 agent. Accordingly, an individual is determined to be responsive or to be maintaining responsiveness (e.g., in some cases when more than one anti-CD47 agent has been administered) when the level of a positive biomarker (i.e., a post-treatment value) in the post-treatment biological sample (or in some cases in multiple post-treatment biological samples) is about 1.5-fold or more (e.g., 2-fold or more, 2.5-fold or more, 3-fold or more, 3.5-fold or more, 4-fold or more, 4.5-fold or more, or 5-fold or more, 8-fold or more, 10-fold or more, 15-fold or more, 20-fold or more, 50-fold or more, 100-fold or more, etc.) greater than the level of the positive biomarker in the pre-treatment biological sample (or than a pre-treatment value).

Because the level of a negative biomarker decreases as a result of administering an anti-CD47 agent when an individual is responsive to the anti-CD47 agent (see working examples below), a decrease in the level of a negative biomarker indicates that the individual is responsive or is maintaining responsiveness to an anti-CD47 agent. Accordingly, an individual is determined to be responsive or to be maintaining responsiveness (e.g., in some cases when more than one anti-CD47 agent has been administered) when the level of a negative biomarker in the pre-treatment biological sample (or the pre-treatment value) is about 1.5-fold or more (e.g., 2-fold or more, 2.5-fold or more, 3-fold or more, 3.5-fold or more, 4-fold or more, 4.5-fold or more, or 5-fold or more, 8-fold or more, 10-fold or more, 15-fold or more, 20-fold or more, 50-fold or more, 100-fold or more, etc.) more than the level of the negative biomarker in the post-treatment biological sample (or in some cases in multiple post-treatment biological samples).

Because the level of a neutral biomarker does not change (or changes minimally) as a result of administering an anti-CD47 agent when an individual is responsive to the anti-CD47 agent (see working examples below), a lack of significant change in the level of a neutral biomarker indicates that the individual is responsive or is maintaining responsiveness to an anti-CD47 agent. Accordingly, an individual is determined to be responsive or to be maintaining responsiveness (e.g., in some cases when more than one anti-CD47 agent has been administered) when the level of a neutral biomarker (i.e., a post-treatment value) in the post-treatment biological sample (or in some cases in multiple post-treatment biological samples) is less than about 5-fold (e.g., less than about 4.5-fold, less than about 4-fold, less than about 3.5-fold, less than about 3-fold, less than about 2.5-fold, less than about 2-fold, or less than about 1.5-fold) greater than the level of the neutral biomarker in the pre-treatment biological sample (or than a pre-treatment value); and when the level of the neutral biomarker in the pre-treatment biological sample (or the pre-treatment value) is less than about 5-fold (e.g., less than about 4.5-fold, less than about 4-fold, less than about 3.5-fold, less than about 3-fold, less than about 2.5-fold, less than about 2-fold, or less than about 1.5-fold) greater than the level of the neutral biomarker in the post-treatment biological sample (or in some cases in multiple post-treatment biological samples).

In some cases, combinations of biomarkers are used in the subject methods. In some such cases, the levels of all measured biomarkers must change (positive or negative biomarkers) or not change (neutral biomarkers) appropriately (as described above) in order for the determination to be made that the individual is responsive or is maintaining responsiveness to an anti-CD47 agent. Otherwise, the individual is determined to be not responsive or to be not maintaining responsiveness to the anti-CD47 agent.

In some embodiments, only positive biomarkers (e.g., 1 to 7, 2 to 7, 3 to 7, 4 to 7, 5 to 7, or 6 to 7 positive biomarkers, e.g., 1, 2, 3, 4, 5, 6, or 7 positive biomarkers) are used (or a single positive biomarker is used). In some cases, two types of biomarker (positive and negative; positive and neutral) are used. In some cases, all three types of biomarker (positive, negative, and neutral) are used. In the above cases, when a positive biomarker is used, any combination of the positive biomarkers may be used. In the above cases, when a neutral biomarker is used, any neutral biomarker(s) (e.g., 1 to 4, 2 to 4, or 3 to 4 neutral biomarkers, e.g., 1, 2, 3, or 4 neutral biomarkers) can be used in any combination.

The term "responsive" as used herein means that the anti-CD47 agent is having the desired effect and the individual's body is responding appropriately to the administration of the anti-CD47 agent. For example, and not to bound by theory, the administration of an anti-CD47 agent is expected to block the interaction between CD47 on a target cell and SIRPα on a phagocytic cell (e.g., macrophage). When this blockage is successful, the body responds in multiple ways, one of which includes the activation of phagocytic cells, which (i) no longer receive "don't eat me" signals from the target cell, (ii) begin to actively phagocytose the target cell, and (iii) secrete (and/or exhibit increased expression of) particular proteins such as positive biomarkers (e.g., MCP-3). The increased level of a positive biomarker is detectable (e.g., the increased level in the blood is detectable as a result of increased secretion). When the individual does not respond appropriately to an anti-CD47 agent, it may be desirable to seek a different therapy or treatment regime for the individual.

The determination that an individual is responsive or not responsive (or is maintaining responsiveness or not maintaining responsiveness) to an anti-CD47 agent is a direct and active clinical application of the correlation between biomarker expression and the activity of an anti-CD47 agent. For example, "determining" requires the active step of reviewing the data, which is produced during the active assaying step(s), and resolving whether an individual is or is not responsive (or maintaining responsiveness). Additionally, in some cases, a decision is made to proceed with the current treatment (i.e., therapy), or instead to alter the treatment. In some cases, the subject methods include the step of continuing therapy or altering therapy.

The term "continue treatment" (i.e., continue therapy) is used herein to mean that the current course of treatment (e.g., continued administration of an anti-CD47 agent) is to continue. For example, if the current course of treatment includes the administration of an anti-CD47 agent at a particular dose and/or with a particular dosing frequency (e.g., once per day, once every other day, etc.), than to "continue therapy" would be to continue administering the anti-CD47 agent at that particular dose and/or with that particular dosing frequency. If the current course of treatment includes a ramping (e.g., decreasing dose and/or frequency over time) of administration of an anti-CD47 agent, then "continue therapy" would mean to continue the ramping (e.g., until the individual is deemed to be non-responsive, at which point the therapy may be altered, e.g., the altered therapy may include an increased dose and/or frequency of an anti-CD47 agent).

Alternatively, "altering therapy" is used herein to mean "discontinuing therapy" or "changing the therapy" (e.g., changing the particular dose and/or frequency of anti-CD47 agent administration, e.g., increasing the dose and/or frequency). In some cases, therapy can be altered, e.g., increased, until a dose and/or frequency is reached at which the individual is deemed to be responsive. In some embodiments, altering therapy means changing which anti-CD47 agent is administered, discontinuing use of any anti-CD47 agent altogether, etc.

As a non-limiting illustrative example, if the current course of treatment is a ramped decrease of frequency of administration an anti-CD47 agent (e.g., the second administration is performed 1 day after the first administration, the third administration is performed 1.5 days after the second administration, the fourth administration is performed 2 days after the third administration, etc), the level of a biomarker may be monitored in order to determine when to discontinue the ramp strategy. Thus, a ramping decrease of dose (and/or ramping decrease of frequency of administration) can be used to establish a minimum effective dose and/or frequency (e.g., a minimum dose and/or minimum frequency of administration at which the individual remains responsive to the anti-CD47 agent). Once the individual becomes non-responsive (or less responsive in some cases), the ramping strategy may be discontinued (i.e., "altered") in favor of the established minimum dose and/or frequency.

As another non-limiting illustrative example, if the current course of treatment is performed at a particular dose and the individual is determined to be non-responsive, then an altered therapy (e.g., increased dose and/or frequency) may be used, and the individual re-tested to determine if they are responsive to the newly changed (e.g., increased) dose and/or frequency of administration. Thus, in some cases, a ramping increased dose and/or frequency strategy (e.g., the second administration is performed at a higher dose than the first, the third is performed at a higher does than the second, etc.) can be used to establish an effective dose of an anti-CD47 agent for the individual. In such cases, when the individual is deemed to be non-responsive, the dose and/or frequency of administration may increase, and when the individual is deemed to be responsive, the dose and/or frequency of administration may stabilize (i.e., will be similar to the most recent dose and/or frequency of administration).

In other words, the level of a biomarker may be monitored in order to determine when to continue therapy and/or when to alter therapy. As such, a post-treatment biological sample can be isolated after any of the administrations and assayed to determine the level of a biomarker. Accordingly, the subject methods can be used to determine whether an individual (an individual being treated for symptoms, illnesses, and/or diseases that can be treated with an anti-CD47 agent) is responsive or is maintaining responsiveness to an anti-CD47 agent. Therefore, the subject methods can be used to determine, for example, whether an individual being treated with an anti-CD47 agent for cancer and/or infection is responsive or is maintaining responsiveness to the anti-CD47 agent.

In some embodiments, determining whether an individual is responsive to an anti-CD47 agent comprises determining whether an individual exhibits a prolonged response to an anti-CD47 agent. In some such cases, an anti-CD47 agent is administered to the individual more than once (e.g., two or more times, three or more times, four or more times, five or more times, etc.). When administered more than once, an anti-CD47 agent can be administered at the same dose or at a different does than previously administered. A post-treatment biological sample can be isolated from an individual after any administration of an anti-CD47 agent. As a non-limiting example, in some cases, a pre-treatment biological sample is isolated from an individual (e.g., on day "0"); an anti-CD47 agent is administered more than once to the individual (e.g., on days "1", "3", "4", "6", and "9"); and a post-treatment biological sample is then isolated (e.g., after the fifth time an anti-CD47 agent is administered).

The anti-CD47 agent can be administered to an individual any time after a pre-treatment biological sample is isolated from the individual, but it is preferable for the anti-CD47 agent to be administered simultaneous with or as soon as possible (e.g., about 7 days or less, about 3 days or less, e.g., 2 days or less, 36 hours or less, 1 day or less, 20 hours or less, 18 hours or less, 12 hours or less, 9 hours or less, 6 hours or less, 3 hours or less, 2.5 hours or less, 2 hours or less, 1.5 hours or less, 1 hour or less, 45 minutes or less, 30 minutes or less, 20 minutes or less, 15 minutes or less, 10 minutes or less, 5 minutes or less, 2 minutes or less, or 1 minute or less) after a pre-treatment biological sample is isolated (or, when multiple pre-treatment biological samples are isolated, after the final pre-treatment biological sample is isolated).

In some cases, a second anti-CD47 agent is administered to the individual. The second anti-CD47 agent can be the same agent and/or same dose as a previously administered anti-CD47 agent. In some cases, the anti-CD47 agent is a different agent and/or a different dose than a previously administered anti-CD47 agent. Any anti-CD47 agent can be administered one or more times as described above and any post-treatment biological sample can be isolated from the individual after any administration of an anti-CD47 agent. Thus, for example, after a first post-treatment biological sample is collected, an anti-CD47 agent can be administered to the individual one or more times and another post-treatment biological sample (e.g., a second, third, fourth, fifth, etc. post-treatment biological sample) can be isolated after any of the administrations of the anti-CD47 agent. When an anti-CD47 agent is administered to an individual more than once or when more than one anti-CD47 agent is administered, each administration of an anti-CD47 agent can take place in a range from about 2 hours to about 8 weeks (e.g., about 2 hours to about 48 hours, about 2 hours to about 36 hours, about 2 hours to about 24 hours, about 2 hours to about 12 hours, about 2 hours to about 6 hours, about 12 hours to about 4 weeks, about 12 hours to about 2 weeks, about 12 hours to about 1 week, about 12 hours to about 2 days, about 12 hours to about 36 hours, about 1 day to about 8 weeks, about 1 day to about 6 weeks, about 1 day to about 4 weeks, about 1 day to about 2 weeks, about 1 day to about 1 week, about 3 days to about 8 weeks, about 3 days to about 6 weeks, about 3 days to about 4 weeks, about 3 days to about 2 weeks, about 3 days to about 1 week, about 1 week to about 8 weeks, about 1 week to about 6 weeks, or about 1 week to about 4 weeks) after a previous administration of an anti-CD47 agent.

In some cases (e.g., where the method is used to determine whether an individual exhibits a prolonged response to an anti-CD47 agent), a post-treatment biological sample is isolated about 1 week or more (e.g., about 1.5 weeks or more, about 2 weeks or more, about 2.5 weeks or more, about 3 weeks or more, about 3.5 weeks or more, about 4 weeks or more, about 5 weeks or more, about 6 weeks or more, about 7 weeks or more, about 8 weeks or more, about 9 weeks or more, about 10 weeks or more, about 11 weeks or more, about 12 weeks or more, etc.) after an anti-CD47 agent is administered (e.g., after the first administration of an anti-CD47 agent), or after a pre-treatment biological sample is isolated.

In some cases (e.g., where the method is used to determine whether an individual exhibits a prolonged response to an anti-CD47 agent), a post-treatment biological sample is isolated in a range from about 2 weeks to about 6 months (e.g., from about 2 weeks to about 5 months, from about 2 weeks to about 4 months, from about 2 weeks to about 3 months, from about 2 weeks to about 2 months, from about 2 weeks to about 1 month, from about 1 month to about 6 months, from about 1 month to about 5 months, from about 1 month to about 4 months, from about 1 month to about 3 months, or from about 1 month to about 2 months) after an anti-CD47 agent is administered (e.g., after the first administration of an anti-CD47 agent), or after a pre-treatment biological sample is isolated.

In some cases, the second biological sample is isolated in a range from about 1 hour to about 2 weeks (e.g., from about 1 hour to about 14 days, from about 3 hours to about 14 days, from about 12 hours to about 14 days, from about 24 hours to about 14 days, from about 3 days to about 14 days, from about 5 days to about 14 days, from about 7 days to about 14 days, from about 10 days to about 14 days, from about 2 hours to about 14 days, from about 2 hours to about 10 days, from about 2 hours to about 7 days, from about 2 hours to about 5 days, from about 2 hours to about 3 days, from about 2 hours to about 2 days, from about 2 hours to about 1 day, from about 6 hours to about 7 days, from about 6 hours to about 5 days, from about 6 hours to about 2 days, from about 6 hours to about 1 day, from about 12 hours to about 7 days, from about 12 hours to about 5 days, from about 12 hours to about 3 days, from about 12 hours to about 2 days, from about 12 hours to about 1 day, from about 1 day to about 14 days, from about 1 day to about 10 days, from about 1 day to about 7 days, from about 1 day to about 5 days, or from about 1 day to about 3 days) after an anti-CD47 agent is administered (e.g., after the first administration of an anti-CD47 agent), or after a pre-treatment biological sample is isolated.

A post-treatment biological sample should be isolated from an individual after enough time has passed to allow for the detection of a change in levels of a biomarker (e.g., a positive biomarker), but not so much time that the effect has time to wear off (e.g., the level of the biomarker returns to baseline). In some embodiments, a post-treatment biological sample is isolated in a range from about 1 hour to about 8 days (e.g., from about 1 hour to about 8 days, from about 1 hour to about 48 hours, from about 1 hour to about 36 hours, from about 1 hour to about 24 hours, from about 1 hour to about 18 hours, from about 1 hour to about 12 hours, from about 1 hour to about 9 hours, from about 1 hour to about 6 hours, from about 1 hour to about 3 hours, from about 1 hour to about 2 hours, from about 2 hours to about 3 hours, from about 3 hours to about 48 hours, from about 3 hours to about 36 hours, from about 3 hours to about 24 hours, from about 3 hours to about 18 hours, from about 3 hours to about 12 hours, from about 3 hours to about 12 hours, from about 3 hours to about 6 hours, from about 12 hours to about 8 days, from about 12 hours to about 7 days, from about 12 hours to about 6 days, from about 12 hours to about 5 days, from about 12 hours to about 4 days, from about 12 hours to about 3 days, from about 12 hours to about 2 days, from about 12 hours to about 36 hours, from about 12 hours to about 1 day, from about 1 day to about 8 days, from about 1 day to about 7 days, from about 1 day to about 6 days, from about 1 day to about 5 days, from about 1 day to about 4 days, from about 1 day to about 3 days, from about 1 day to about 2 days, about 1 hour, about 2 hours, about 3 hours, about 6 hours, about 9 hours, about 12 hours, about 18 hours, about 24 hours, about 36 hours, about 2 days, about 3 days, about 4 days, about 5 days, about 6 days, about 7 days, or about 8 days) after administering an anti-CD47 agent to the individual.

In some embodiments, the subject methods include providing an analysis indicating whether the individual is determined to be responsive or not responsive to the anti-CD47 agent, or whether the individual is determined to be maintaining responsiveness or not maintaining responsiveness to the anti-CD47 agent. As described above, an analysis can be an oral or written report (e.g., written or electronic document). The analysis can be provided to the subject, to the subject's physician, to a testing facility, etc. The analysis can also be accessible as a website address via the internet. In some such cases, the analysis can be accessible by multiple different entities (e.g., the subject, the subject's physician, a testing facility, etc.).

Administering an Anti-CD47 Agent.

Suitable anti-CD47 agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an anti-CD47 agent includes use in combination with another therapeutic agent (e.g., another anti-infection agent or another anti-cancer agent). Therapeutic formulations comprising one or more anti-CD47 agents of the invention are prepared for storage by mixing the anti-CD47 agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The anti-CD47 agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The anti-CD47 agent can be "administered" by any suitable means, including topical, oral, parenteral, intrapulmonary, and intranasal. Parenteral infusions include intramuscular, intravenous (bollus or slow drip), intraarterial, intraperitoneal, intrathecal or subcutaneous administration.

The anti-CD47 agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An anti-CD47 agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent by non-covalent associations, such as non-covalent bonding or by encapsulation. The nature of the carrier can be either soluble or insoluble for purposes of the invention. Those skilled in the art will know of other suitable carriers for binding anti-CD47 agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent through an acceptable chemical linker or chelation carrier. Positron emitting moieties for use in the present invention include $^{18}F$, which can be easily conjugated by a fluorination reaction with the anti-CD47 agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-CD47 agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing a therapeutic dosage range for use in humans. The exact formulation, route of administration and dosage can be chosen by the individual physician in view of the patient's condition.

Suitable administration of an anti-CD47 agent (e.g., a therapeutically effective dose) can entail administration of a single dose, or can entail administration of doses daily, semi-weekly, weekly, once every two weeks, once a month, annually, etc. Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., and the like.

For more information on administering an anti-CD47 agent, see patent application 61/800,102 (Methods for Achieving Therapeutically Effective Doses of anti-CD47 Agents), which is hereby incorporated by reference in its entirety.

Kits

Also provided are kits for use in the methods. The subject kits include a tool (e.g., a PCR primer pair specific for a biomarker, an antibody that specifically binds to a biomarker, and the like) for determining the level of at least one positive biomarker. A kit can also include a tool for determining the level of a negative and/or a neutral biomarker. In some embodiments, a kit comprises tools for determining the level of two or more different biomarkers (e.g., two different positive biomarkers; a positive biomarker and a neutral biomarker; a positive biomarker and a negative biomarker, and the like).

The subject kits can also include an anti-CD47 agent. An anti-CD47 agent can be provided in a dosage form (e.g., a therapeutically effective dosage form). In some embodiments, an anti-CD47 agent is provided in two or more different dosage forms (e.g., two or more different therapeutically effective dosage forms). In the context of a kit, an anti-CD47 agent can be provided in liquid or solid form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility

The subject methods and kits can be used to monitor an individual's responsiveness to the administration of an anti-CD47 agent, which can be used to treat any infliction where the target cells (e.g., cancer cells, infected cells, etc.) exhibit an increased expression of CD47 relative to normal cells of the same type. The anti-CD47 agent that is administered inhibits the interaction between SIRPα (e.g., on a phagocyte) and CD47 on a target cell (e.g., on a cancer cell, on an infected cell, etc.), thereby increasing in vivo phagocytosis of the target cell, and an associated response (e.g., an increase in the expression of positive biomarkers). Thus, the levels of the biomarkers described herein can be used to determine whether an individual exhibits responsiveness to treatment with an anti-CD47 agent.

In some embodiments the infliction is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral and lentiviral pathogens, e.g. HIV-1; HIV-2, HTLV, FIV, SIV, etc. Hepatitis B virus, etc. Microbes of interest, but not limited to the following, include: *Yersinia* sp., e.g. *Y. pestis, Y. pseudotuberculosis, Y enterocolitica; Franciscella* sp.; *Pasturella* sp.; *Vibrio* sp., e.g. *V. cholerae, V. parahemolyticus; Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc. Also included are intracellular protozoan pathogens, e.g. *Plasmodium* sp, *Trypanosoma* sp., *Giardia* sp., *Toxoplasma* sp., *Leishmania* sp., etc.

An infection treated with the methods of the invention generally involves a pathogen with at least a portion of its life-cycle within a host cell, i.e. an intracellular phase. The methods of the invention provide for a more effective removal of infected cells by the phagocytic cells of the host organism, relative to phagocytosis in the absence of treatment, and thus are directed to the intracellular phase of the pathogen life cycle.

In some embodiments, the methods of the invention include diagnosis of a patient as suffering from a pathogenic intracellular infection; or selection of a patient previously diagnosed as suffering from a pathogenic intracellular infection; treating the patient with a regimen of anti-CD47 therapy, optionally in combination with an additional therapy; assaying a post-treatment biological sample for the level of a biomarker; and/or monitoring the patient for efficacy of treatment. Monitoring may measure clinical indicia of infection, e.g. fever, white blood cell count, etc., and/or direct monitoring for presence of the pathogen.

Treatment may be combined with other active agents. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment. In some cases, treatment is combined with other active agents as a result of the subject methods. For example, if an individual is determined to be not responsive to an anti-CD47 agent, an alteration in therapy may include combining the administration of the anti-CD47 agent with another active agent.

In some embodiments the infliction is cancer. As noted above, any cancer in which a cancerous cell expresses an increased level of CD47 relative to a non-cancerous cell of the same type can be treated with the subject methods.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

Cancers and cancer cells that can be treated include, but are not limited to, hematological cancers, including leukemia, lymphoma and myeloma, and solid cancers, including for example tumors of the brain (glioblastomas, medulloblastoma, astrocytoma, oligodendroglioma, ependymomas), carcinomas, e.g. carcinoma of the lung, liver, thyroid, bone, adrenal, spleen, kidney, lymph node, small intestine, pancreas, colon, stomach, breast, endometrium, prostate, testicle, ovary, skin, head and neck, and esophagus.

In an embodiment, the cancer is a hematological cancer. In an embodiment, the hematological cancer is a leukemia. In another embodiment, the hematological cancer is a myeloma. In an embodiment, the hematological cancer is a lymphoma.

In an embodiment, the leukemia is selected from acute myeloid leukemia (AML), acute lymphocytic leukemia (ALL), chronic lymphocytic leukemia (CLL) and chronic myelogenous leukemia (CML). In an embodiment, the leukemia is AML. In an embodiment, the leukemia is ALL. In an embodiment, the leukemia is CLL. In a further embodiment, the leukemia is CML. In an embodiment, the cancer cell is a leukemic cell, for example, but not limited to, an AML cell, an ALL cell, a CLL cell or a CML cell.

Suitable cancers that can be responsive to treatment using an anti-CD47 agent include without limitation leukemia; acute myeloid leukemia (AML); acute lymphoblastic leukemia (ALL); metastasis; minimal residual disease; solid tumor cancers, e.g., breast, bladder, colon, ovarian, glioblastoma, leiomyosarcoma, and head & neck squamous cell carcinomas; etc. For examples, see: (i) Willingham et al., Proc Natl Acad Sci USA. 2012 Apr. 24; 109(17):6662-7: "The CD47-signal regulatory protein alpha (SIRPα) interaction is a therapeutic target for human solid tumors"; (ii) Edris et al., Proc Natl Acad Sci USA. 2012 Apr. 24; 109(17):6656-61: "Antibody therapy targeting the CD47 protein is effective in a model of aggressive metastatic leiomyosarcoma"; and (iii) US patent application 20110014119; all of which are herein incorporated in their entirety.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Examples

Figure 1B:
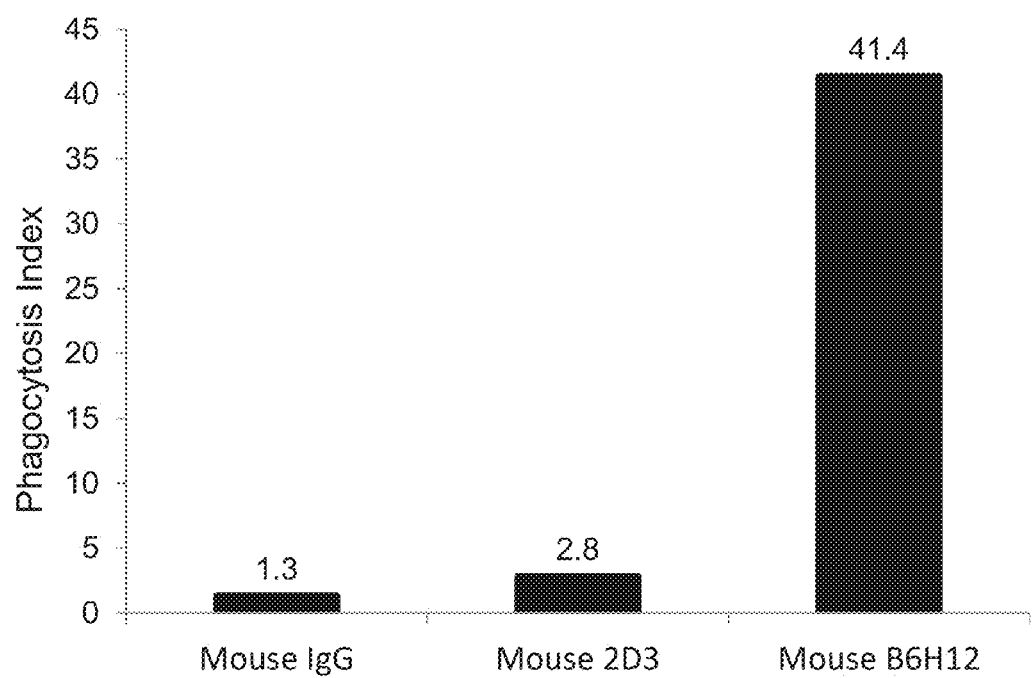

Phagocytosis of cancer cells caused by anti-CD47 agents was verified (FIG. 1). A. Depicted are representative images of in vitro phagocytosis assays performed with DLD-1 human colon cancer cells and primary human macrophages. Basal levels of phagocytosis were observed with isotype control antibody (mIgG1) or non-blocking anti-CD47 antibody (clone m2D3), and elevated levels were observed with CD47-blocking antibody (clone mB6H12). Images taken at 200× magnification. B. Quantification of phagocytosis in response to anti-CD47 antibodies from A. Phagocytosis index defined as number of tumor cells engulfed by 100 macrophages.

Figures 2A, 2B:
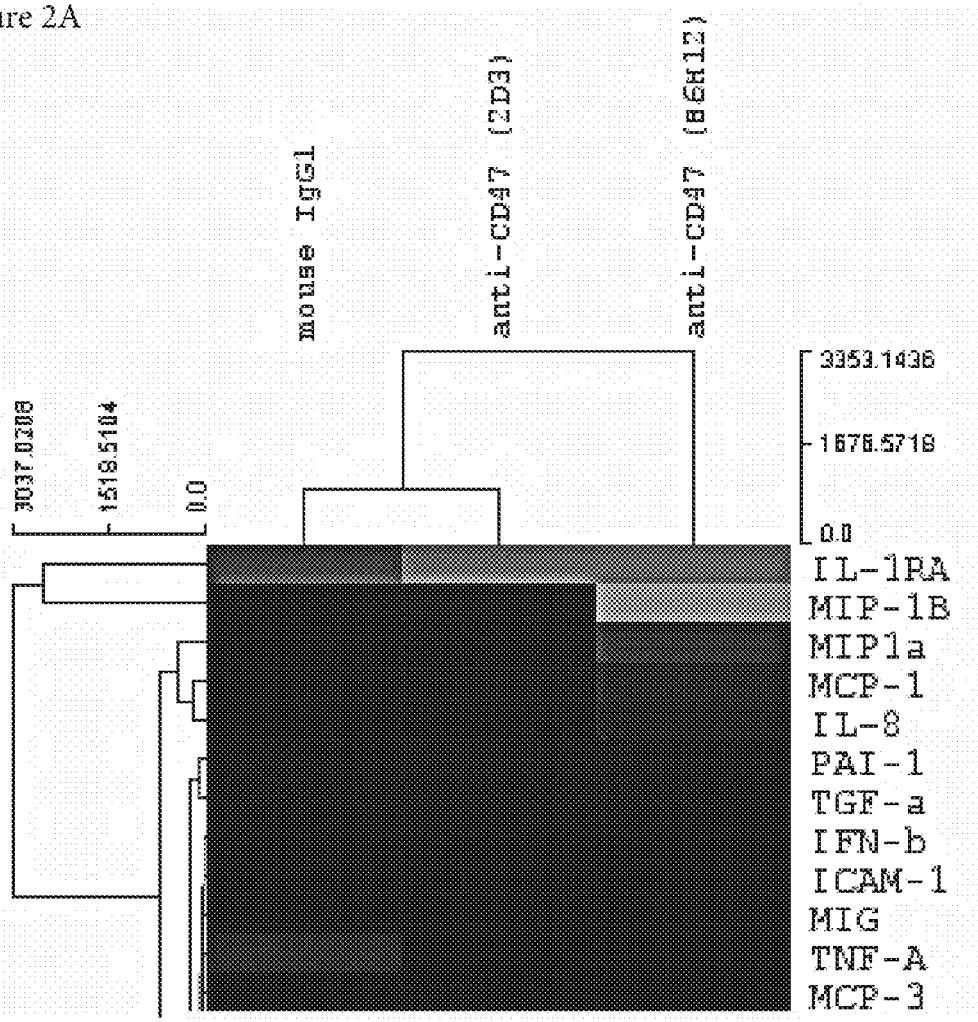
FIG. 2A-2B Human macrophages secreted a specific cytokine signature in response to anti-CD47 agents (CD47-blocking agents).
Figure 3A:
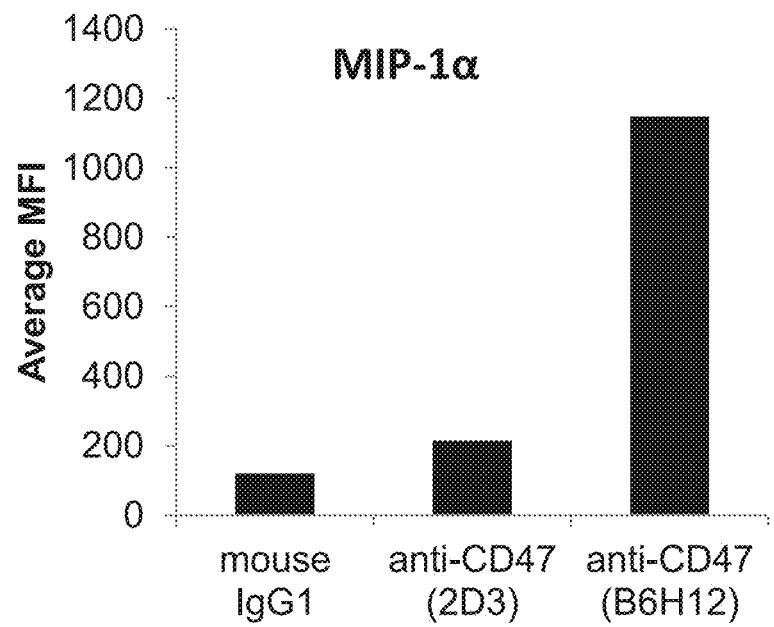
FIG. 3A-3C Specific cytokines were secreted by human macrophages in response to anti-CD47 mediated phagocytosis.
Figure 3A:
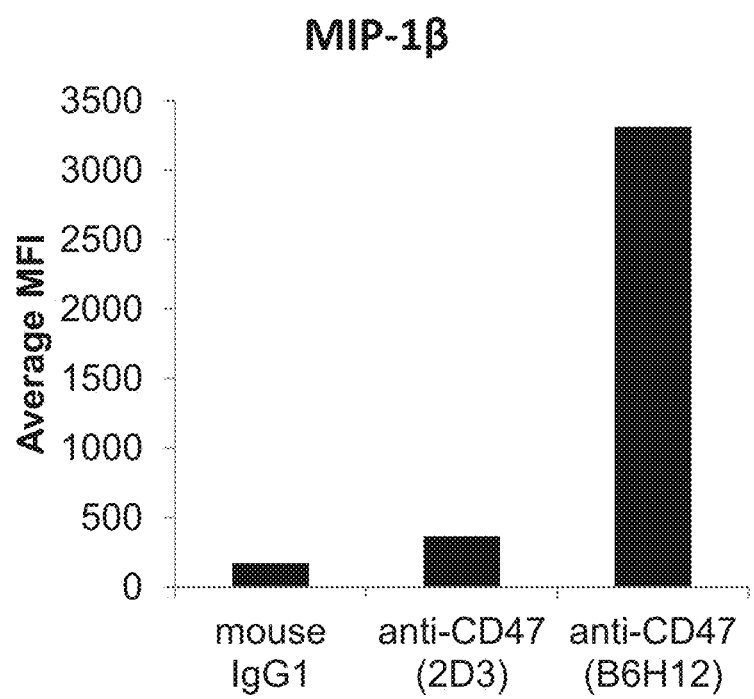
Figure 3B:
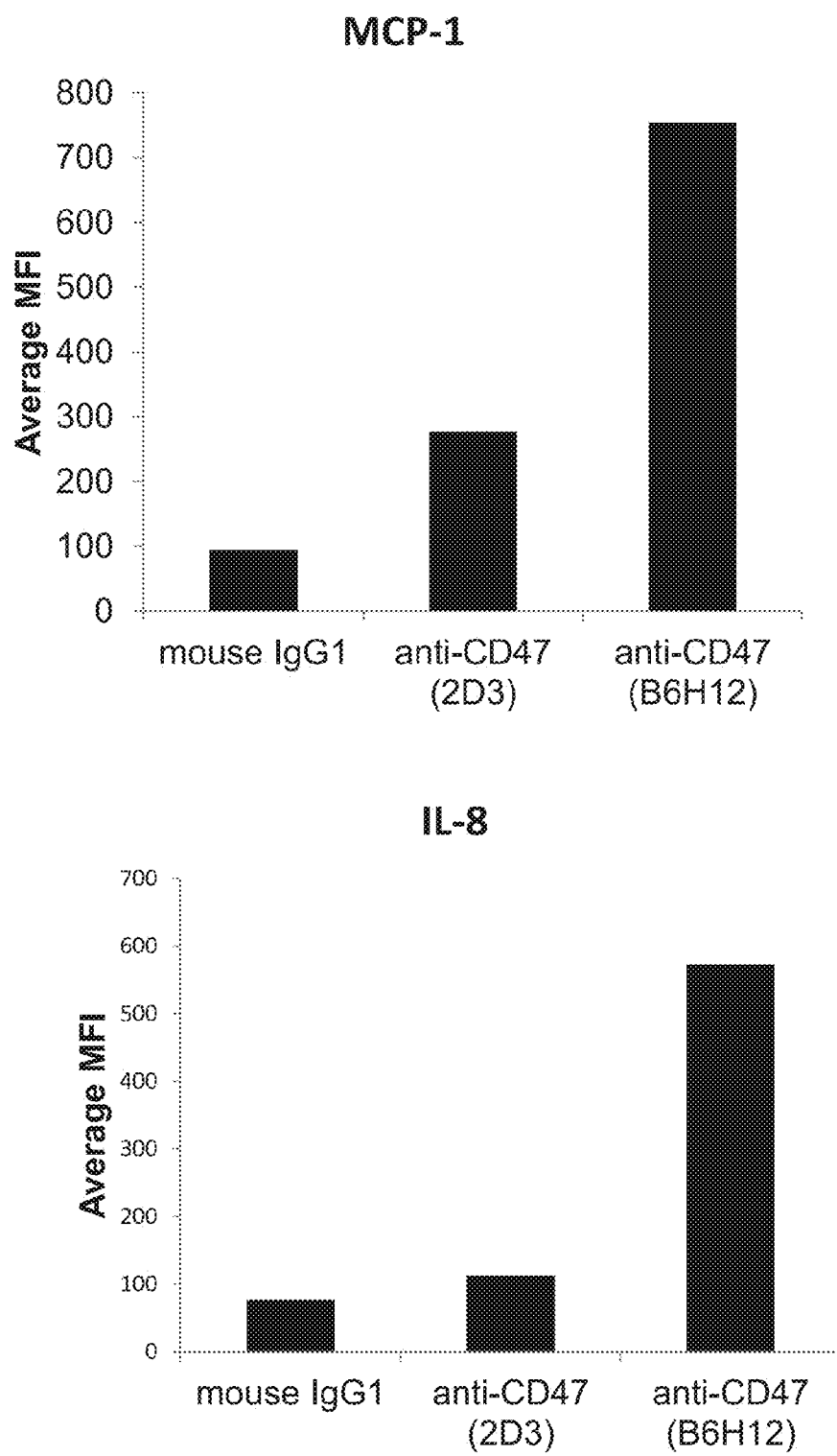
Figure 3C:
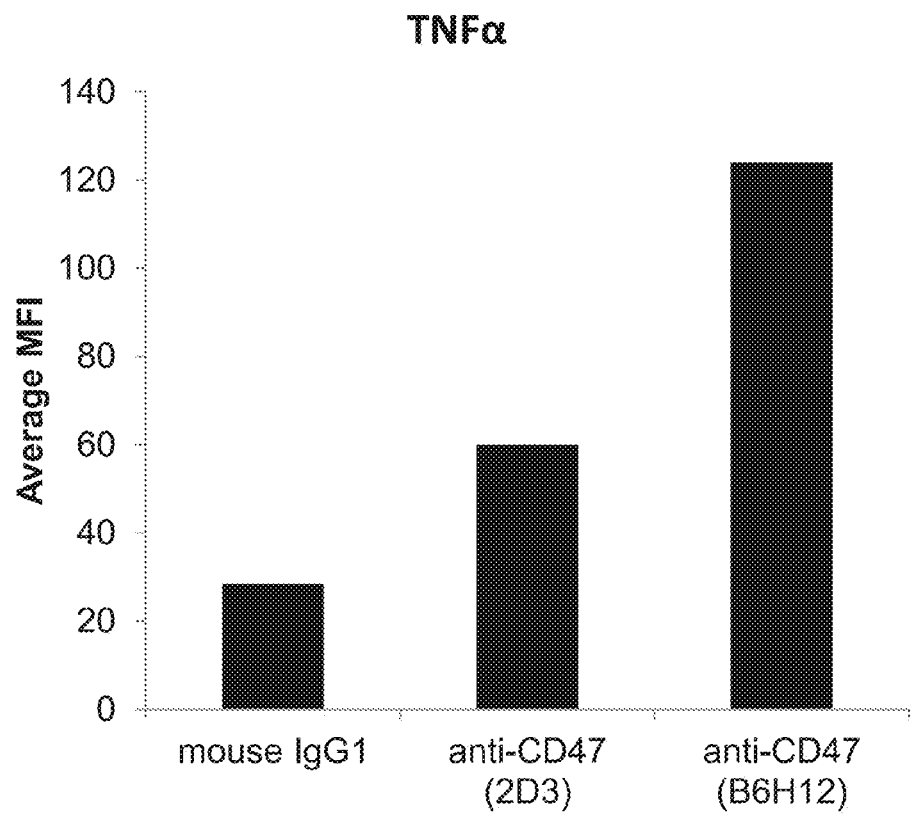
Figure 3C:
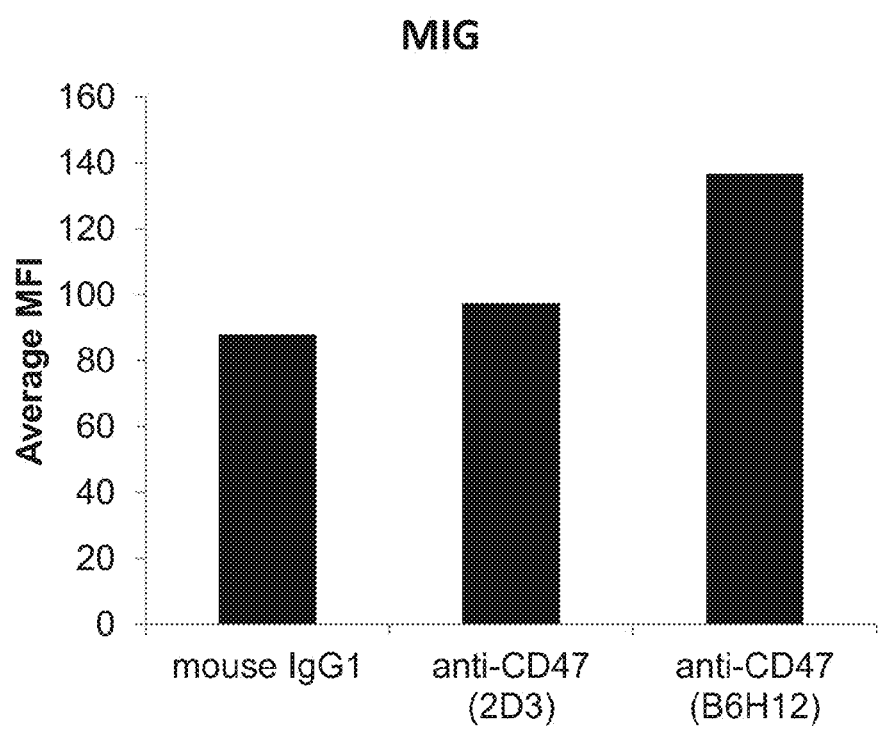

Human macrophages were found to secrete a specific cytokine signature in response to CD47-blocking agents (FIG. 2). A. Cytokines were measured that were secreted by human macrophages in vitro after phagocytosis of DLD-1 human colon cancer cells in response to anti CD47 agents. Lighter shades indicate higher levels of cytokine secretion, with MIP-1β, MIP-1α, MCP-1, and IL-8 forming a cluster of cytokines secreted specifically in response to the CD47-blocking antibody clone B6H12. Cytokines were simultaneously measured from tissue culture supernatants by Luminex® multiplex array. B. Cytokines measured in phagocytosis assays with human macrophages as described in A, for which levels did not change in response to anti-CD47 agents.

Specific cytokines were secreted by human macrophages in response to anti-CD47 mediated phagocytosis (FIG. 3). Cytokines were measured by Luminex® multiplex array from supernatants of phagocytosis assays performed with human macrophages and DLD-1 human colon cancer cells. Mean fluorescence intensity (MFI) indicates relative cytokine concentrations. A. MIP-1α and MIP-1β, B. MCP-1 (CCL2) and IL-8, and C. TNFα and MIG are specifically secreted by human macrophages in response to anti-CD47 (CD47-blocking antibody clone B6H12) mediated phagocytosis of DLD-1 human colon cancer cells.

Figure 4:
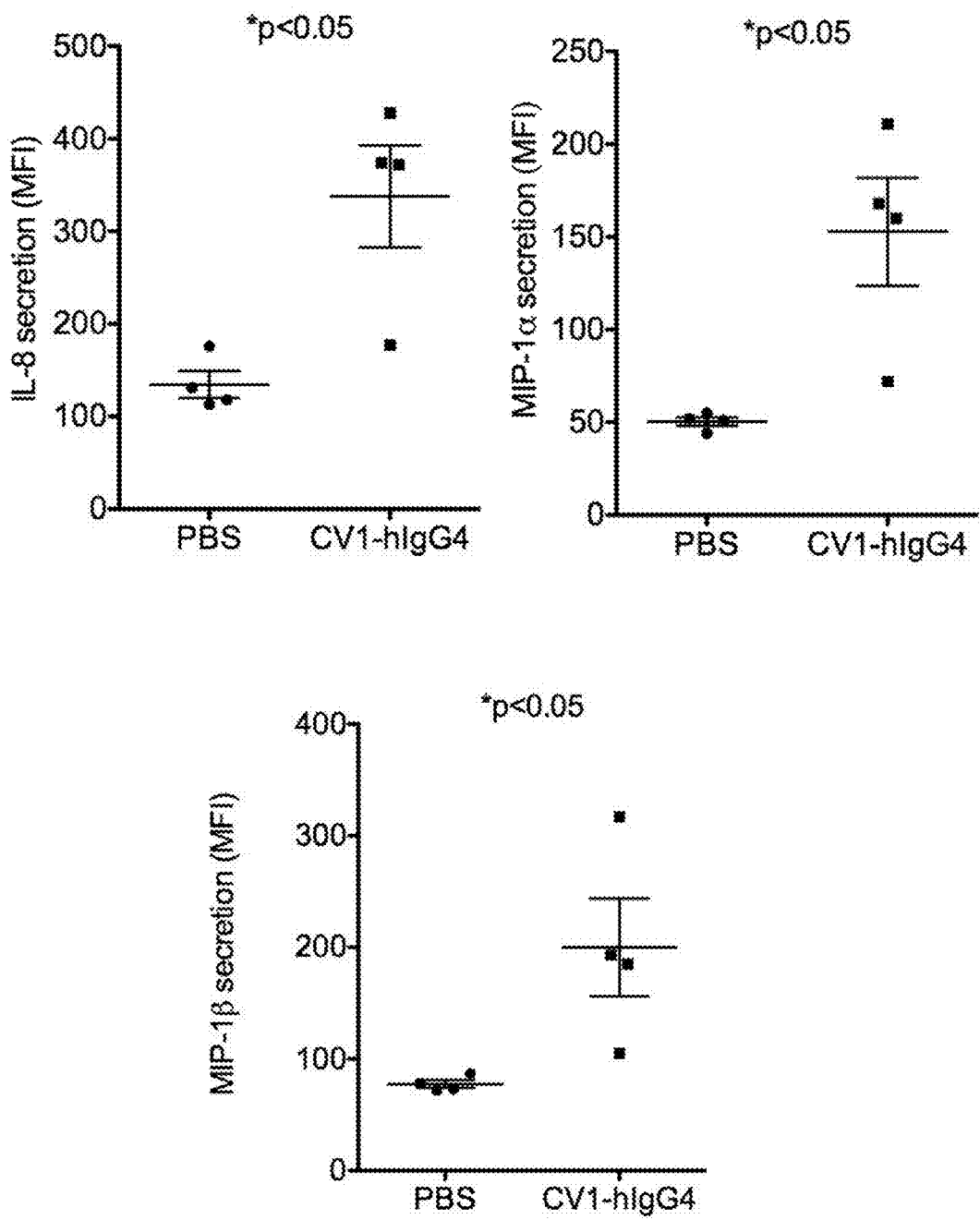
FIG. 4 Cytokines were secreted in response high-affinity SIRPα fusion protein CV1-hIgG4 (an anti-CD47 agent).

Cytokines were secreted in response high-affinity SIRPα fusion protein CV1-hIgG4 (an anti-CD47 agent) (FIG. 4). In vitro phagocytosis assays were performed with primary human macrophages and DLD-1 human colon cancer cells. Cytokine levels were measured by Luminex® multiplex array. Mean fluorescence intensity (MFI) indicates relative cytokine concentrations in the supernatant. Elevated IL-8, MIP-1α, and MIP-1β were observed. Bars indicate mean±SD. Individual points show measurements form independent human macrophage donors.

Figure 5:
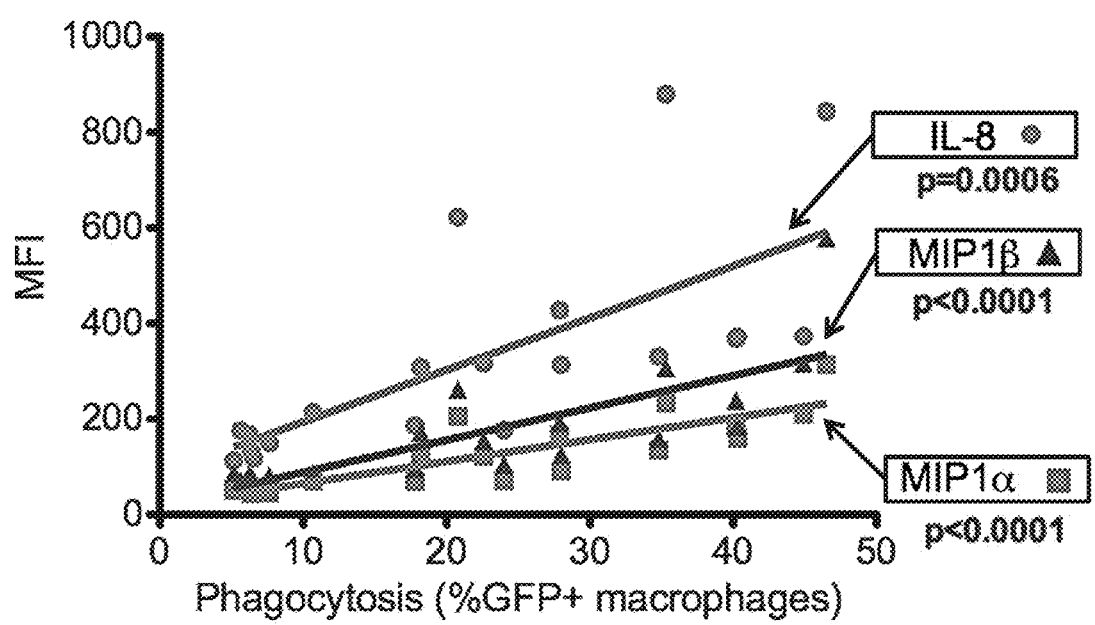
FIG. 5 Cytokines secreted by human macrophages in response to anti-CD47 agents correlated with levels of phagocytosis.

Cytokines secreted by human macrophages in response to anti-CD47 agents correlated with levels of phagocytosis (FIG. 5). In vitro phagocytosis assays were performed with human macrophages and DLD-1 human colon cancer cells treated with varying concentrations of the anti-CD47 agents CV1-hIgG4 or chimeric anti-CD47 clone B6H12 (hIgG4). Phagocytosis was measured by flow cytometry as the percentage of macrophages engulfing GFP+ DLD-1 human colon cancer cells (% GFP+ macrophages). Levels of phagocytosis showed a positive correlation with secreted IL-8, MIP-1α, and MIP-1β in the supernatant. Mean fluorescence intensity (MFI) indicates relative cytokine concentrations in the supernatant.

Figure 6:
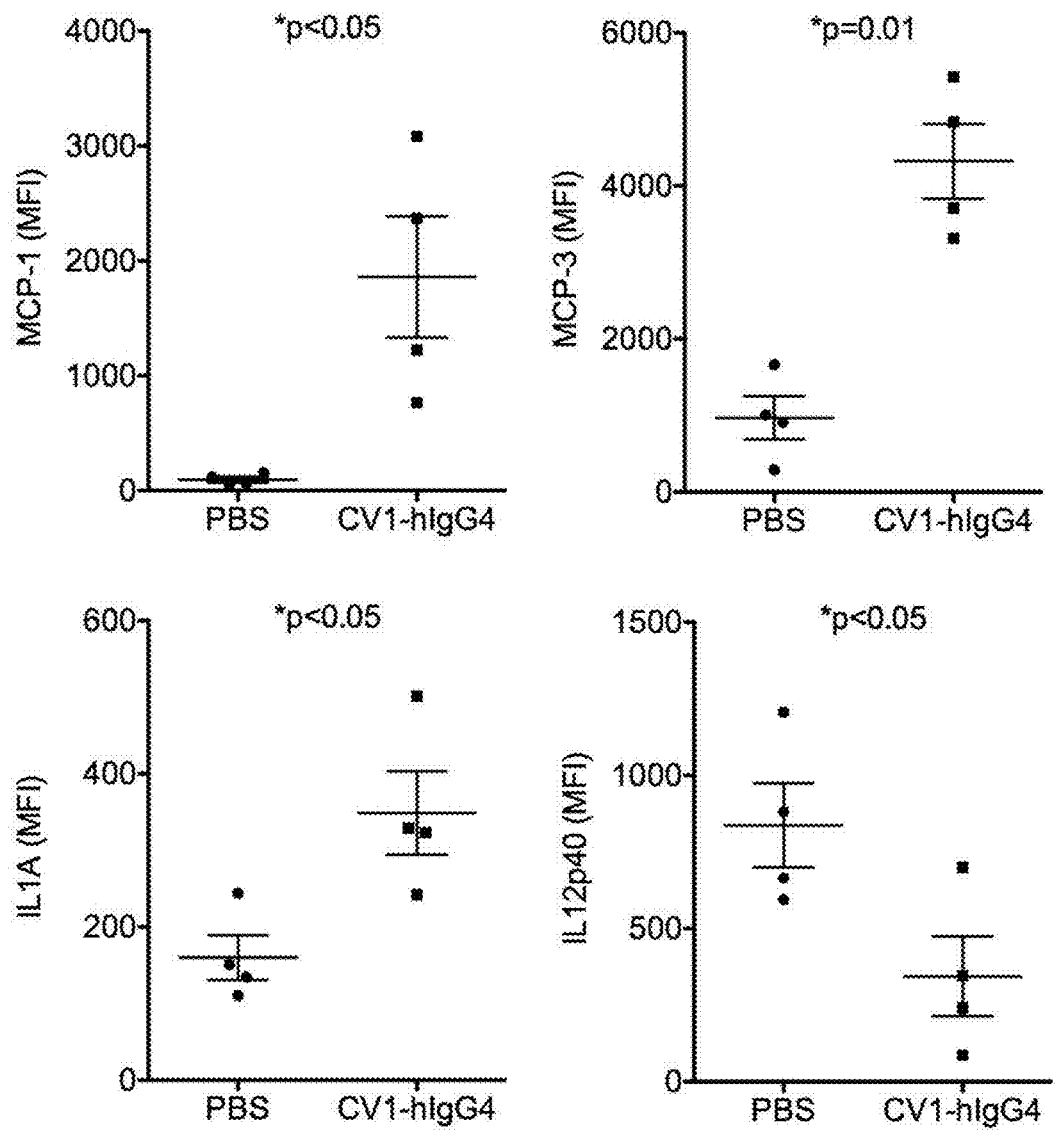
FIG. 6 Treatment of tumor-bearing mice with an anti-CD47 agent induced changes in cytokine levels.

Treatment of tumor-bearing mice with an anti-CD47 agent induced changes in cytokine levels (FIG. 6). NSG mice were engrafted intraperitoneally with human colon cancer cells (DLD-1). Malignant ascites were allowed to form, and mice were then randomized into two treatment cohorts of four mice. Mice were given a single treatment of vehicle control (PBS) or 500 ug CV1-hIgG4. 24 hours post-treatment, ascites fluid was collected from the mice, clarified by centrifugation, and analyzed by Mouse Luminex® cytokine array. Mean fluorescence intensity (MFI) indicated relative cytokine concentrations in the supernatant. MCP-1, MCP-3 and IL1A were elevated in response to CV1-hIgG4, while IL12p40 decreased. Bars indicate mean±SD. Individual points represent values from independent mice.

Figure 7:
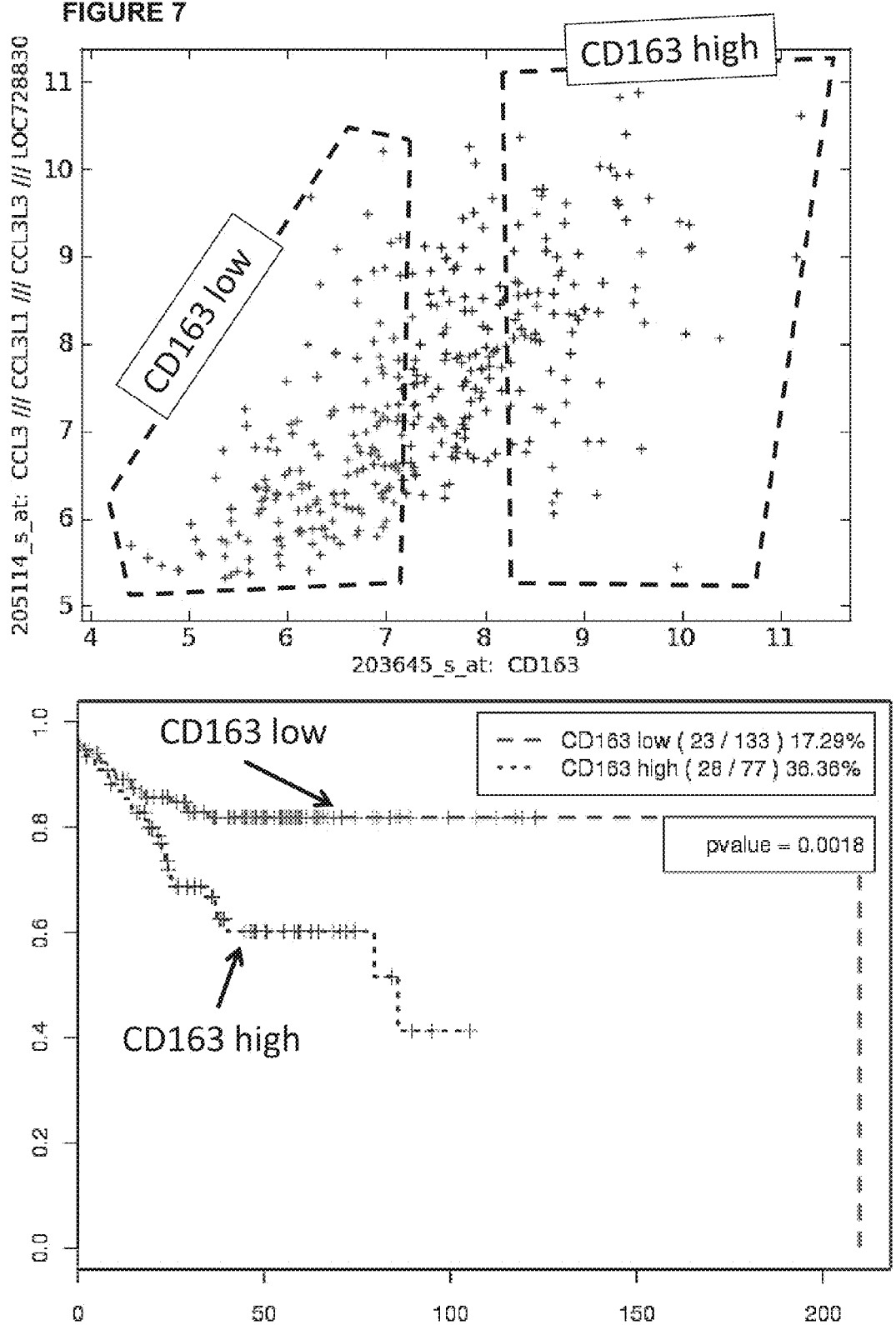
FIG. 7 CD163 RNA expression correlated with poor prognosis in human colon cancer patients.

CD163 RNA expression correlated with poor prognosis in human colon cancer patients (FIG. 7). Macrophages frequently infiltrate tumors, and CD163 is an established marker of tumor-associated macrophages. In colon cancer, RNA expression of CD163, a surrogate for macrophages, correlates with poor patient outcome. Data analyzed from Jorissen+Smith Colon Merged Data Sets (n=355). Upper panel: normalized RNA levels of CD163 (x-axis) versus MIP1a (CCL3; y-axis). Boxes outlined by hashed lines indicate CD163 low and high populations that were compared for survival. Lower panel: Kaplan-Meier plot showing overall survival of colon cancer patients exhibiting a CD163 low or CD163 state. X-axis depicts time in months, Y-axis depicts fractional survival (1.0=100%).

Figure 8:
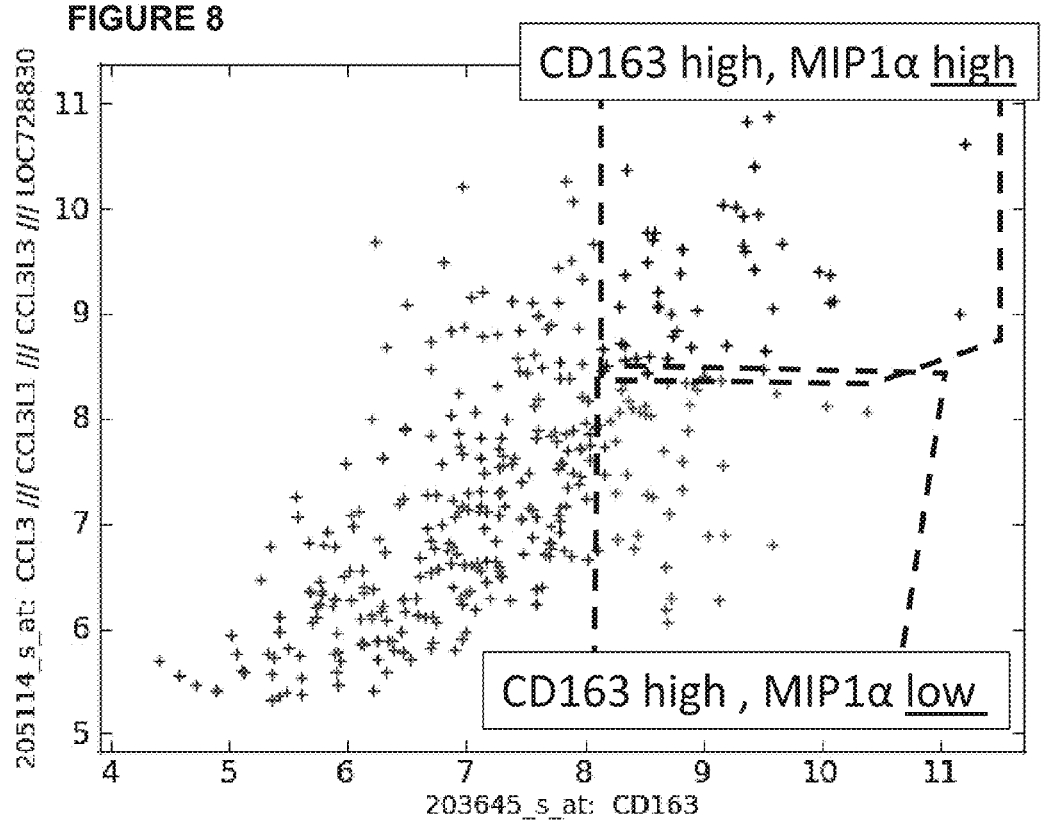
FIG. 8 MIP-1α RNA expression correlated with favorable prognosis in human colon cancer patients with elevated CD163 levels.
Figure 8:
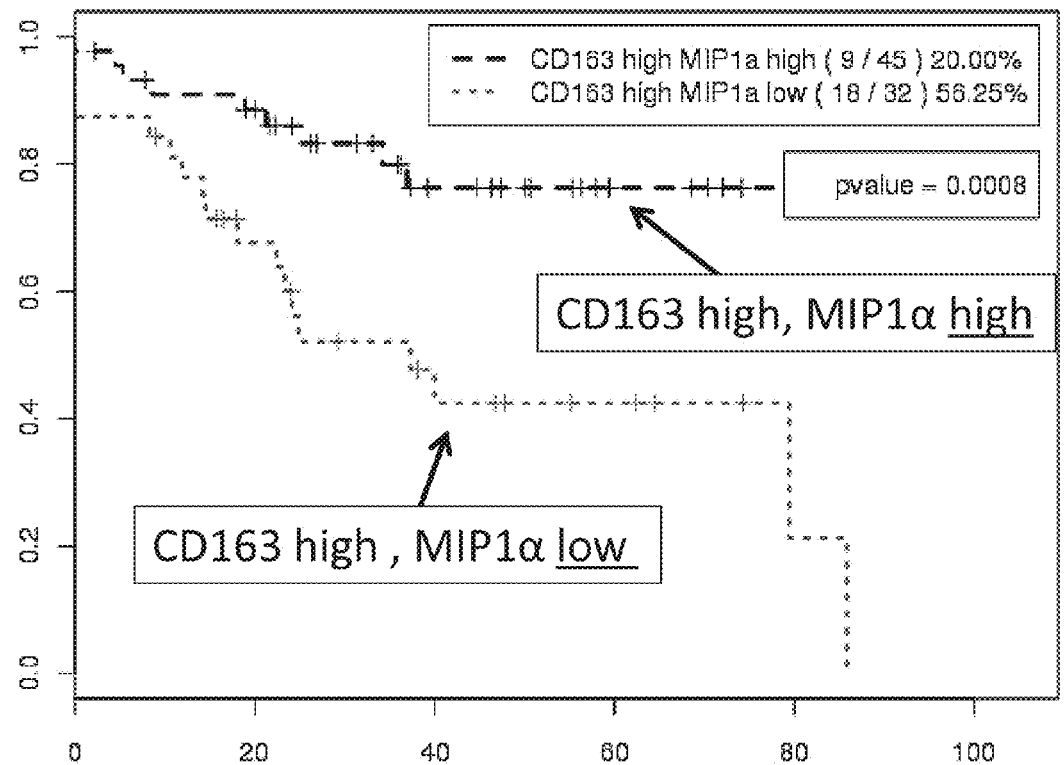

MIP-1α RNA expression correlated with favorable prognosis in human colon cancer patients with elevated CD163 levels (FIG. 8). In tumors exhibiting elevated CD163 expression, a surrogate for macrophage infiltration, co-expression of MIP-1α correlated with prolonged survival. Without being bound to theory, since MIP-1α is correlated with human macrophage phagocytosis, co-expression of high levels of CD163 and MIP-1α indicate a state where an extensive macrophage infiltrate is actively attacking and phagocytosing tumor cells, thus giving rise to a favorable prognosis and suggesting MIP-1α levels can have diagnostic and prognostic value when evaluated in human patients. Data was analyzed from Jorissen and Smith Colon Merged Data Sets (Jorissen et al., 2009 Clin Cancer Res 15:7642-7651: "Metastasis-associated gene expression changes predict poor outcomes in patients with dukes stage B and C colorectal cancer"; and Smith et al., 2009 Gastroenterology 138: 958-968: "Experimentally derived metastasis gene expression profile predicts recurrence and death in patients with colon cancer"). Upper panel: normalized RNA levels of CD163 (x-axis) versus MIP-1α (CCL3; y-axis). Boxes outlined by hashed lines indicate CD163 high, MIP-1α high and CD163 high, MIP-1α low populations that were compared for survival. Lower panel: Kaplan-Meier plot showing overall survival of colon cancer patients exhibiting a CD163 high, MIP-1α high or CD163 high, MIP-1α low phenotype. X-axis depicts time in months; Y-axis depicts survival ratio (1.0=100% survival).

Figure 9:
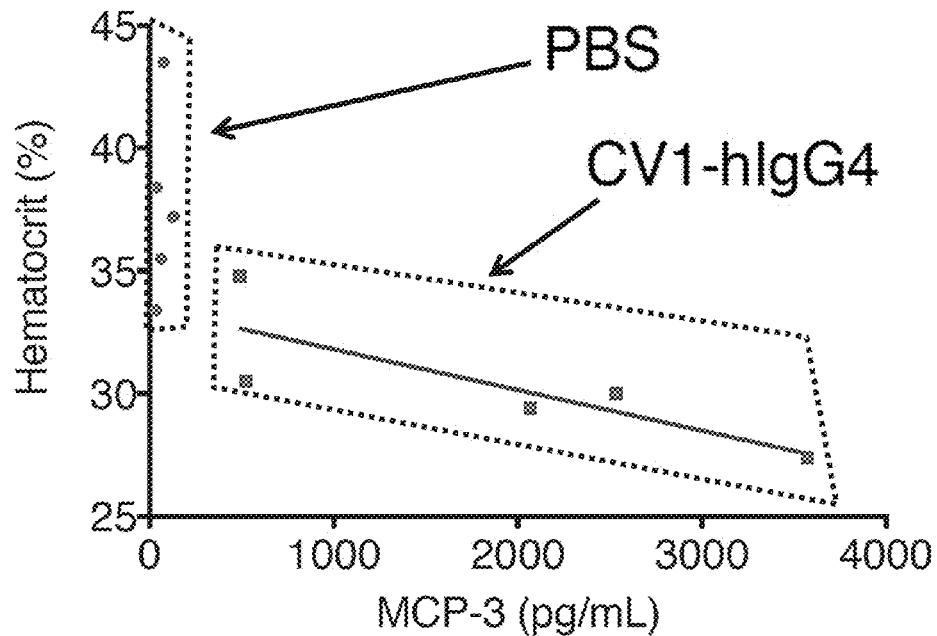
FIG. 9 In mice engrafted with human bladder cancer, treatment with CD47-blocking agents induced elevated MCP-3 levels in the serum that correlated with a drop in hematocrit.

In mice engrafted with human bladder cancer, treatment with CD47-blocking agents induced elevated MCP-3 levels in the serum that correlated with a drop in hematocrit (FIG. 9). CD47-targeted therapies result in phagocytosis of tumor cells and also normal red blood cells expressing CD47. Since CV1-hIgG4 binds and blocks CD47 on both mouse and human cells, it causes a moderate drop in hematocrit in mice upon treatment. Elevated drops in hematocrit are indicative of greater macrophage phagocytosis in response to therapy, and MCP-3 levels in the serum correlated with the drop in hematocrit. MCP-3 levels were measured by Luminex® multiplex array from serum samples of mice bearing 639-V human bladder cancer after daily treatment with CV1-hIgG4 for 25 days.

Figure 10:
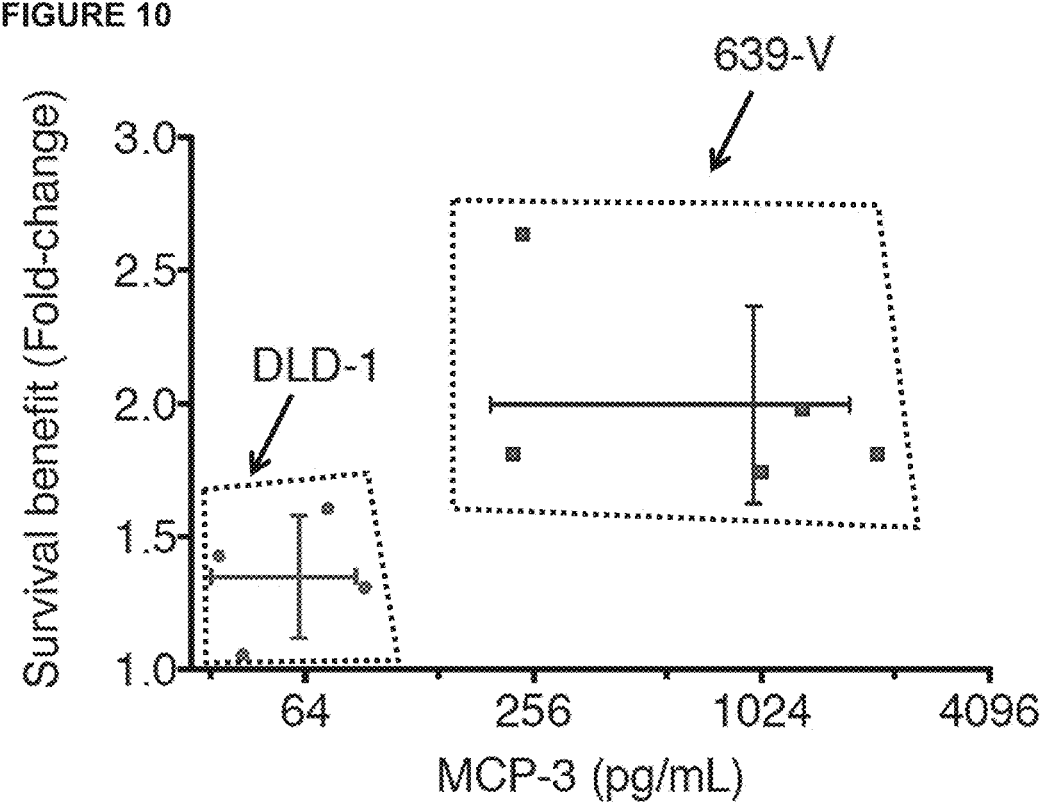
FIG. 10 MCP-3 serum levels were indicative of greater benefits in survival in mice (bearing human cancers) treated with CD47-blocking agents.

MCP-3 serum levels were indicative of greater benefits in survival in mice (bearing human cancers) treated with CD47-blocking agents (FIG. 10). Mice engrafted with DLD-1 human colon cancer (circles) or 639-V human bladder cancer (squares) were treated with daily injections of CV1-hIgG4. Serum levels of MCP-3 were measured by Luminex® array. Survival benefit defined as fold-change over average survival of control tumor-bearing mice treated with vehicle. Serum MCP-3 levels were measured after 19 days (DLD-1 bearing mice) or 25 days (639-V bearing mice) of treatment. Sustained elevation of MCP-3 levels led to a greater benefit in survival (Compare 639-V bladder cancer bearing mice to DLD-1 colon cancer bearing mice). X-axis is depicted in Log 2 scale.

Figure 11:
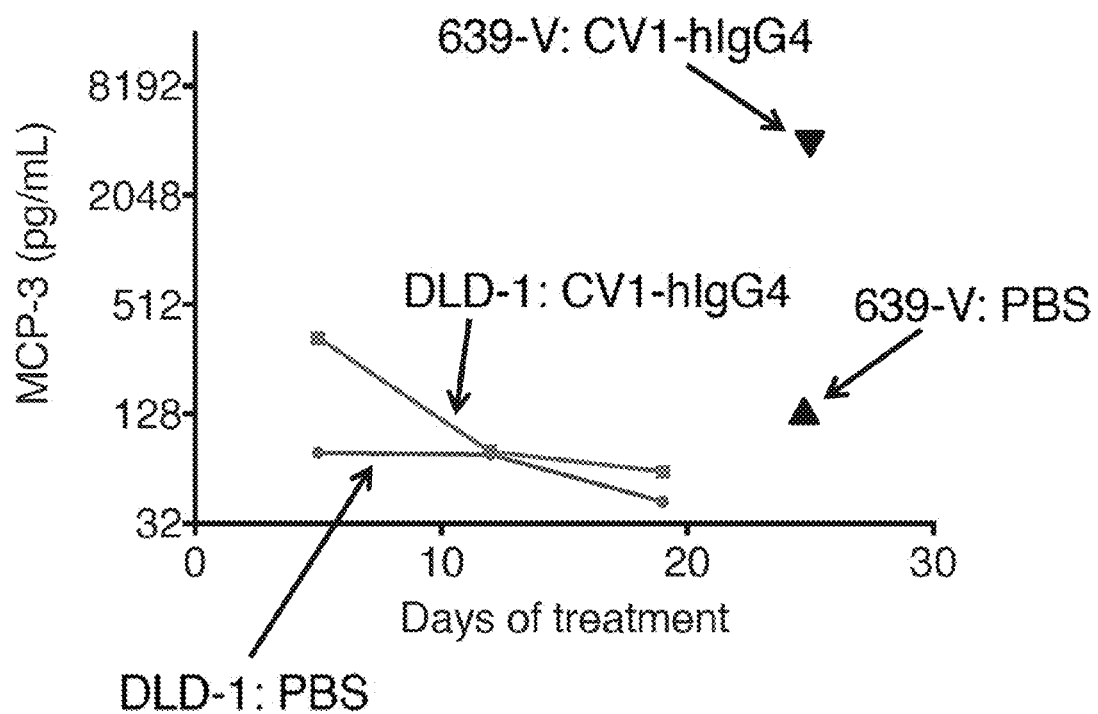
FIG. 11 Sustained MCP-3 serum levels correlated with greater survival of tumor-bearing mice.

Sustained MCP-3 serum levels correlated with greater survival of tumor-bearing mice (FIG. 11). Mice bearing DLD-1 human colon cancer (gray) were treated with vehicle (PBS, circles) or CV1-hIgG4 (squares) and MCP-3 levels were measured over time. MCP-3 levels were initially elevated but decreased over time, despite continued treatment. Thus, DLD-1 colon cancer bearing mice exhibited MCP-3 levels that were not elevated after prolonged treatment, and they exhibited poor survival compared to mice bearing 639-V bladder cancer (FIG. 10). Mice bearing 639-V human bladder cancer (black) were treated with vehicle (PBS, upward triangle) or CV1-hIgG4 (downward triangle) and serum MCP-3 was measured after 25 days of treatment. 639-V bearing animals treated with CV1-hIgG4 exhibited elevated levels of MCP-3 after prolonged treatment, which correlated with a greater benefit in survival compared to DLD-1 tumor bearing mice (FIG. 10).

What is claimed is:

1. A method of determining whether an individual is responsive to an anti-Cluster-of-Differentiation-47 (CD47) agent, the method comprising:
administering the anti-CD47 agent, wherein the anti-CD47 agent is a CD47 blocking antibody, an anti-Signal-Regulatory-Protein-α (SIRPα) antibody, a SIRPα polypeptide that binds to human CD47 and blocks the interaction between CD47 and SIRPα, or a soluble CD47 polypeptide, to the individual after isolating a pre-treatment biological sample, and before isolating a post-treatment biological sample of the same type of biological sample, wherein the biological sample is selected from a blood sample, a serum sample, a plasma sample, a bone marrow sample, a biopsy sample, a fine needle aspirate, a lymph node aspirate, a cystic aspirate, a paracentesis sample, a thoracentesis sample;
assaying the pre-treatment and post-treatment biological samples to determine the level of a positive biomarker Macrophage Inflammatory Protein-1 alpha/Chemokine (C-C) motif ligand 3 (MIP-1α/CCL3); and
determining that the individual is responsive to the anti-CD47 agent when the level of the positive biomarker in the post-treatment biological sample is about 1.5-fold or more greater than the level of the positive biomarker in the pre-treatment biological sample, or determining that the individual is not responsive to the anti-CD47 agent when the level of the positive biomarker in the post-treatment biological sample is less than about 1.5-fold greater than the level of the positive biomarker in the pre-treatment biological sample.

2. The method according to claim 1, wherein the post-treatment biological sample is isolated in a range from about 1 hour to about 8 days after the anti-CD47 agent is administered to the individual.

3. The method according to claim 1, wherein the anti-CD47 agent is administered two or more times.

4. The method according to claim 3, wherein the post-treatment biological sample is isolated about 2 weeks or more after the first administration of the anti-CD47 agent.

5. The method according to claim 1, wherein the assaying steps comprise measuring the extracellular level of the positive biomarker protein.

6. The method according to claim 1, further comprising:
providing an analysis indicating whether the individual is determined to be responsive or not responsive to the anti-CD47 agent.

7. The method according to claim 1, further comprising:
assaying each of the pre-treatment and post-treatment biological samples to determine the level of a neutral biomarker, wherein the neutral biomarker is selected from the group consisting of: Interleukin-12 P70 (IL12P70), Interleukin-1 beta (IL-1β), Interleukin-6 (IL-6), Tumor necrosis factor alpha (TNFα), and a combination thereof.

8. The method according to claim 1, further comprising:
continuing therapy when the individual is determined to be responsive to the anti-CD47 agent, or altering therapy when the individual is determined to be not responsive to the anti-CD47 agent.

9. A method of determining whether an individual is maintaining responsiveness to an anti-CD47 agent wherein the anti-CD47 agent is a CD47 blocking antibody, an anti-SIRPα antibody, a SIRPα polypeptide that binds to human CD47 and blocks the interaction between CD47 and SIRPα, or a soluble CD47 polypeptide, the method comprising:
assaying a pre-treatment biological sample, a first post-treatment biological sample, and a second post-treatment biological sample of the same type from an individual treated with a first anti-CD47 agent, to determine the level of positive biomarker Macrophage Inflammatory Protein-1 alpha (MIP-1α) (MIP-1α), wherein the biological sample is selected from a blood sample, a serum sample, a plasma sample, a bone marrow sample, a biopsy sample, a fine needle aspirate, a lymph node aspirate, a cystic aspirate, a paracentesis sample, a thoracentesis sample; and
determining that the individual is maintaining responsiveness to the anti-CD47 agent when the level of the positive biomarker in each of the first and second post-treatment biological samples is about 1.5-fold or more greater than the level of the positive biomarker in the pre-treatment biological sample, or determining that the individual is not maintaining responsiveness to the anti-CD47 agent when the level of the positive biomarker in each of the first and second post-treatment biological samples is less than about 1.5-fold greater than the level of the positive biomarker in the pre-treatment biological sample.

10. The method according to claim 9, wherein a second anti-CD47 agent is administered in a range from about 1 week to about 5 weeks after the first anti-CD47 agent is administered.

11. The method according to claim 10, wherein the first post-treatment biological sample is isolated in a range from about 1 hour to about 8 days after the first anti-CD47 agent is administered, and wherein the second post-treatment biological sample is isolated in a range from about 1 hour to about 8 days after the second anti-CD47 agent is administered.

12. The method according to claim 9, wherein the first and second anti-CD47 agents are the same agent.

13. The method according to claim 9, wherein the second post-treatment biological sample is isolated about 2 weeks or more after the first anti-CD47 agent is administered.

14. The method according to claim 9, wherein:
(i) the first anti-CD47 agent is administered more than once prior to the isolation of the first post-treatment biological sample;

(ii) the second anti-CD47 agent is administered more than once prior to the isolation of the second post-treatment biological; or both (i) and (ii).

15. The method according to claim 9, further comprising assaying the pre-treatment biological sample and the first and second post-treatment biological samples to determine the level of a neutral biomarker, wherein the neutral biomarker is selected from a group consisting of: Interleukin-12 P70 (IL12P70), Interleukin-1 beta (IL-1β), Interleukin-6 (IL-6), Tumor necrosis factor alpha (TNFα), and a combination thereof.

16. The method of claim 1, wherein the positive biomarker is MIP-1α (CCL3).

17. The method according to claim 1, wherein the pre-treatment and post-treatment biological samples are a blood sample or a derivative thereof.

18. The method according to claim 1, wherein the pre-treatment and post-treatment biological samples are a serum sample.

19. The method according to claim 9, wherein the pre-treatment and post-treatment biological samples are a blood sample or a derivative thereof.

20. The method according to claim 9, wherein the pre-treatment and post-treatment biological samples are a serum sample.

* * * * *

SEQUENCE LISTING

```
<160> NUMBER OF SEQ ID NOS: 11

<210> SEQ ID NO 1
<211> LENGTH: 99
<212> TYPE: PRT
<213> ORGANISM: Homo Sapiens

<400> SEQUENCE: 1

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

<210> SEQ ID NO 2
<211> LENGTH: 99
<212> TYPE: PRT
<213> ORGANISM: Homo Sapiens

<400> SEQUENCE: 2

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 3
<211> LENGTH: 271
<212> TYPE: PRT
<213> ORGANISM: Homo Sapiens
```

```
<400> SEQUENCE: 3

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
                100                 105                 110

Ser Ala Pro Phe Ser Phe Leu Ser Asn Val Lys Tyr Asn Phe Met Arg
            115                 120                 125

Ile Ile Lys Tyr Glu Phe Ile Leu Asn Asp Ala Leu Asn Gln Ser Ile
130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 4
<211> LENGTH: 99
<212> TYPE: PRT
<213> ORGANISM: Homo Sapiens

<400> SEQUENCE: 4

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95
```

Glu Asn Ser

<210> SEQ ID NO 5
<211> LENGTH: 92
<212> TYPE: PRT
<213> ORGANISM: Homo Sapiens

<400> SEQUENCE: 5

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 6
<211> LENGTH: 92
<212> TYPE: PRT
<213> ORGANISM: Homo Sapiens

<400> SEQUENCE: 6

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 7
<211> LENGTH: 125
<212> TYPE: PRT
<213> ORGANISM: Homo Sapiens

<400> SEQUENCE: 7

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
                20                  25                  30

Cys Ile Ser Thr Asn Gln Gly Thr Ile His Leu Gln Ser Leu Lys Asp
            35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys

```
                        85                  90                  95
Lys Lys Gln Lys Asn Gly Lys Lys His Gln Lys Lys Val Leu Lys
                100                 105                 110
Val Arg Lys Ser Gln Arg Ser Arg Gln Lys Lys Thr Thr
                115                 120                 125

<210> SEQ ID NO 8
<211> LENGTH: 328
<212> TYPE: PRT
<213> ORGANISM: Homo Sapiens

<400> SEQUENCE: 8

Met Cys His Gln Gln Leu Val Ile Ser Trp Phe Ser Leu Val Phe Leu
1               5                   10                  15
Ala Ser Pro Leu Val Ala Ile Trp Glu Leu Lys Lys Asp Val Tyr Val
                20                  25                  30
Val Glu Leu Asp Trp Tyr Pro Asp Ala Pro Gly Glu Met Val Val Leu
                35                  40                  45
Thr Cys Asp Thr Pro Glu Glu Asp Gly Ile Thr Trp Thr Leu Asp Gln
                50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Val
                85                  90                  95
Leu Ser His Ser Leu Leu Leu Leu His Lys Lys Glu Asp Gly Ile Trp
                100                 105                 110
Ser Thr Asp Ile Leu Lys Asp Gln Lys Glu Pro Lys Asn Lys Thr Phe
                115                 120                 125
Leu Arg Cys Glu Ala Lys Asn Tyr Ser Gly Arg Phe Thr Cys Trp Trp
                130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
                180                 185                 190
Cys Gln Glu Asp Ser Ala Cys Pro Ala Ala Glu Glu Ser Leu Pro Ile
                195                 200                 205
Glu Val Met Val Asp Ala Val His Lys Leu Lys Tyr Glu Asn Tyr Thr
                210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
                260                 265                 270
Phe Cys Val Gln Val Gln Gly Lys Ser Lys Arg Glu Lys Lys Asp Arg
                275                 280                 285
Val Phe Thr Asp Lys Thr Ser Ala Thr Val Ile Cys Arg Lys Asn Ala
                290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser
                325
```

<210> SEQ ID NO 9
<211> LENGTH: 269
<212> TYPE: PRT
<213> ORGANISM: Homo Sapiens

<400> SEQUENCE: 9

Met Ala Glu Val Pro Glu Leu Ala Ser Glu Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 10
<211> LENGTH: 212
<212> TYPE: PRT
<213> ORGANISM: Homo Sapiens

<400> SEQUENCE: 10

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
50                  55                  60

```
Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
            130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
210

<210> SEQ ID NO 11
<211> LENGTH: 233
<212> TYPE: PRT
<213> ORGANISM: Homo Sapiens

<400> SEQUENCE: 11

Met Ser Thr Glu Ser Met Ile Arg Asp Val Glu Leu Ala Glu Glu Ala
  1               5                  10                  15

Leu Pro Lys Lys Thr Gly Gly Pro Gln Gly Ser Arg Arg Cys Leu Phe
                 20                  25                  30

Leu Ser Leu Phe Ser Phe Leu Ile Val Ala Gly Ala Thr Thr Leu Phe
             35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190
```

```
Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```